US011819376B2

(12) United States Patent
Giegerich

(10) Patent No.: US 11,819,376 B2
(45) Date of Patent: Nov. 21, 2023

(54) ANALYSIS AND PREDICTION MODEL FOR ORTHODONTIC TREATMENT

(71) Applicant: Alta Smiles LLC, Fort Washington, PA (US)

(72) Inventor: Gary D. Giegerich, Fort Washington, PA (US)

(73) Assignee: ALTA SMILES LLC, Fort Washington, PA (US)

( * ) Notice: Subject to any disclaimer, the term of this patent is extended or adjusted under 35 U.S.C. 154(b) by 0 days.

(21) Appl. No.: 17/611,589

(22) PCT Filed: May 14, 2020

(86) PCT No.: PCT/US2020/032838
§ 371 (c)(1),
(2) Date: Nov. 16, 2021

(87) PCT Pub. No.: WO2020/232223
PCT Pub. Date: Nov. 19, 2020

(65) Prior Publication Data
US 2022/0202530 A1 Jun. 30, 2022

Related U.S. Application Data

(60) Provisional application No. 62/848,807, filed on May 16, 2019.

(51) Int. Cl.
*A61C 7/00* (2006.01)
*G16H 50/50* (2018.01)
(Continued)

(52) U.S. Cl.
CPC ............ *A61C 7/002* (2013.01); *A61C 9/0046* (2013.01); *A61C 9/0053* (2013.01); *G16H 10/60* (2018.01);
(Continued)

(58) Field of Classification Search
None
See application file for complete search history.

(56) References Cited

U.S. PATENT DOCUMENTS 6,688,885 B1 * 2/2004 Sachdeva ................. A61C 7/00
433/24
8,930,219 B2 * 1/2015 Trosien ................... G06Q 10/10
705/2
(Continued)

FOREIGN PATENT DOCUMENTS

AU 2015202831 A1 * 12/2015 ............... A61B 6/14
EP 3050534 B1 4/2018
(Continued)

OTHER PUBLICATIONS

Shah, Anjali B. "Decision Support and Training System for Management of Endodontically Treated Teeth." Order No. 3685672 Rutgers The State University of New Jersey, School of Health Related Professions, 2015. Ann Arbor: ProQuest. Web. Jul. 19, 2023. (Year: 2015).*

(Continued)

*Primary Examiner* — Lena Najarian
(74) *Attorney, Agent, or Firm* — Panitch Schwarze Belisario & Nadel LLP

(57) ABSTRACT

A system for providing orthodontic treatment to a patient wherein a general dentist receives direction from a consultant orthodontist. The system includes a network configured to assign the consultant orthodontist to the general dentist. The network includes a central server with a patient database. The patient database includes a first patient's dental record of a first patient and a plurality of additional patients' historical dental records of a plurality of additional patients. The network also includes an analysis and prediction module. The analysis and prediction module is configured to access the first patient's dental record and the plurality of (Continued)

FIG. 1B additional patients' historical dental records prior to initiation of treatment of the first patient to compare and contrast similar dental records of the additional patients' historical dental records to the first patient's dental records to predict timing and outcome for dental treatment of the first patient.

11 Claims, 18 Drawing Sheets

(51) Int. Cl.
| | | |
|---|---|---|
| *G16H 10/60* | (2018.01) | |
| *G16H 30/20* | (2018.01) | |
| *G16H 20/00* | (2018.01) | |
| *G16H 30/40* | (2018.01) | |
| *G16H 80/00* | (2018.01) | |
| *A61C 9/00* | (2006.01) | |

(52) U.S. Cl.
CPC ............. *G16H 20/00* (2018.01); *G16H 30/20* (2018.01); *G16H 30/40* (2018.01); *G16H 50/50* (2018.01); *G16H 80/00* (2018.01)

(56) References Cited

U.S. PATENT DOCUMENTS

| | | |
|---|---|---|
| 2002/0172911 A1 | 11/2002 | Cooper |
| 2004/0029068 A1 | 2/2004 | Sachdeva et al. |
| 2004/0115586 A1 | 6/2004 | Andreiko et al. |
| 2007/0026363 A1 | 2/2007 | Lehmann et al. |
| 2014/0329194 A1* | 11/2014 | Sachdeva ............... A61C 7/002 433/24 |
| 2017/0360531 A1 | 12/2017 | Janzadeh et al. |
| 2019/0026598 A1 | 1/2019 | Salah et al. |
| 2019/0328489 A1 | 10/2019 | Capron-Richard et al. |
| 2020/0000551 A1* | 1/2020 | Li ......................... G16H 50/50 |

FOREIGN PATENT DOCUMENTS

| | | |
|---|---|---|
| EP | 4046587 A1 | 8/2022 |
| JP | 2010-532681 A | 10/2010 |
| WO | 2018/122557 A2 | 7/2018 |

OTHER PUBLICATIONS

Int'l Preliminary Report on Patentability dated Nov. 25, 2021 in Int'l Application No. PCT/US2020/032838.

Interntional Search Report and Written Opinion for PCT/US20/32838 dated May 14, 2020.

Embracing Novel Technologies in Dentistry and Orthodontics, vol. 56 of the Craniofacial Growth Series, Burcu Bayirli, Mar. 2019.

Extended European Search Report dated Mar. 9, 2023 for Application No. EP 20 805 229.0.

* cited by examiner

ANALYSIS AND PREDICTION MODEL FOR ORTHODONTIC TREATMENT

CROSS-REFERENCE TO RELATED APPLICATIONS

The present application is a Section 371 national phase application of International Patent Application No. PCT/US2020/032838, filed May 14, 2020 and titled, "Analysis and Prediction Model for Orthodontic Treatment" and claims the benefit of U.S. Provisional Patent Application No. 62/848,807, filed May 16, 2019 and titled, "Analysis and Prediction Model for Orthodontic Treatment," the entire contents of which are incorporated herein by reference in their entirety.

BACKGROUND OF THE INVENTION

Orthodontia, orthodontics or dentofacial orthopedics is a specialty of dentistry that deals with the diagnosis, prevention and correction of malpositioned teeth and jaws. Orthodontia is typically conducted at a specialized orthodontist office that handles only orthodontic procedures. Such orthodontic appointments require relatively frequent visits by a patient to the specialized orthodontist office, while also continuing to attend typical dental treatment at their general dentist.

It would be desirable to design, develop and deploy a system and method that facilitates orthodontic procedures at the office of a general dentist under the supervision of a consultant orthodontic specialist in a hub and spoke-type approach. The preferred present invention addresses the shortcomings of the known orthodontic system and method.

BRIEF SUMMARY OF THE INVENTION

Briefly, one aspect of the preferred invention is directed to a system for providing orthodontic treatment to a patient wherein a general dentist receives direction from a consultant orthodontist. The system includes a network configured to assign the consultant orthodontist to the general dentist. The network includes a central server with a patient database. The patient database includes a first patient's dental record of a first patient and a plurality of additional patients' historical dental records of a plurality of additional patients. The network also includes an analysis and prediction module. The analysis and prediction module is configured to access the first patient's dental record and the plurality of additional patients' historical dental records prior to initiation of treatment of the first patient to compare and contrast similar dental records of the additional patients' historical dental records to the first patient's dental records to predict timing and outcome for dental treatment of the first patient.

Another aspect of the preferred invention is directed to a system for providing orthodontic treatment to a patient, wherein a general dentist receives direction from a consultant orthodontist. The system has an imaging device configured to capture at least one image of arches of a first patient, a first communication device configured to control the imaging device and display the at least one image for the general dentist, a network configured to transmit the at least one image to a remote location, and a second communication device connected to the network. The consultant orthodontist is in communication with the remote location. The second communication device is configured to display the at least one image transmitted by the network for the consultant orthodontist or to provide the images to the central processor for analysis and development of a treatment plan by the consultant orthodontist or the central processor.

Another aspect of the preferred invention is directed to a method for providing orthodontic treatment to a patient, wherein a general dentist receives direction from a consultant orthodontist. The method includes capturing, at a first appointment, at least one image of arches of a first patient with an imaging device at a first location associated with the general dentist, displaying the at least one image on a first communication device at the first location, transmitting the at least one image via a network to a second location associated with the consultant orthodontist, receiving or displaying the at least one image on a second communication device at the second location, determining, by a consulting orthodontist at the second location, a treatment plan based on the at least one image, transmitting the treatment plan to the first communication device at the first location and applying, by the general dentist at the first location, dental hardware to one or more of the teeth of the arches of the first patient.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1A:
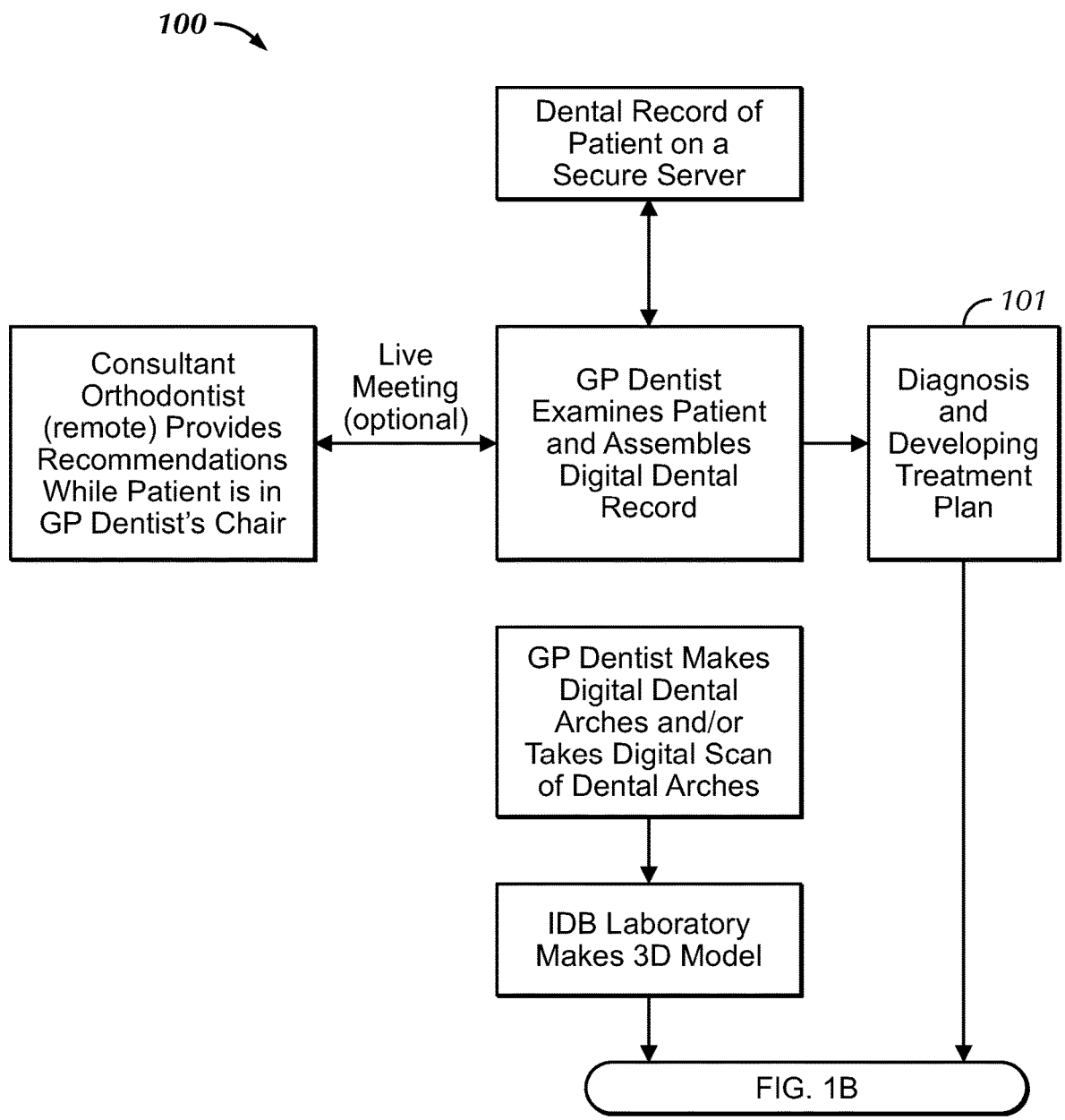
FIGS. 1A and 1B are a schematic representation of a method for providing orthodontic services to a patient in accordance with a first preferred embodiment of the present invention.

Certain terminology is used in the following description for convenience only and is not limiting. Unless specifically set forth herein, the terms "a", "an" and "the" are not limited to one element but instead should be read as meaning "at least one". The words "right," "left," "lower," and "upper" designate directions in the drawings to which reference is made. The words "inwardly" or "distally" and "outwardly" or "proximally" refer to directions toward and away from, respectively, the geometric center or orientation of the device, orthodontic hardware and instruments and related parts thereof. The terminology includes the above-listed words, derivatives thereof and words of similar import.

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIGS. 1-10, the preferred invention is directed to systems 300, 400 and methods 100, 200 for an analysis and prediction model for orthodontic treatment. The preferred methods 100, 200 and systems 300, 400 involve, among other steps and features, taking images of a patient's arches, which may include the patient's teeth, jaw, mouth and related features that may be helpful for the general dentist 306, 406 or consultant orthodontist 305, 405 to view for treatment of the patient 304, storing the images in a database, transmitting the stored images to a consultant orthodontist 305, 405 who analyzes the images, and prescribes treatment methods for the patient based on the consultant orthodontist's 305, 405 analysis and measuring outcomes based on the prescribed treatment. The images may be taken during the initial consultation with the patient by the general dentist 306, 406, may be taken by the patient before the initial consultation and transmitted to the database or may be otherwise obtained for the patient's initial or subsequent consultation. The images and additional information maintained or transmitted by the preferred systems 300, 400 may be stored at a general dentist's 306, 406 location, at a consultant orthodontist's 305, 405 location or at a third party location in a central server, network or central database 301, 302, 401, 402. The general dentist 306, 406, as used herein, also refers to the general dentist's 306, 406 staff, technicians, dental assistants, hygienist and related employees. The consultant orthodontist 305, 405 is preferably remotely located from the general dentist 306, 406 and is not necessarily a human orthodontist, but may be comprised of the networks 301, 401 and an analysis and prediction module 307, 407 that is able to recommend and predict outcomes of the patient 304, 404 being treated based on historical dental records of the patient 304, 404 being treated. The prediction module 307, 407 is also able to recommend a gauge for arch wires 504, placement of the brackets 503 on specific teeth, use of intra-arch elastics, including sizes, materials and stiffnesses, use of luggage loops to rotate teeth, use of common tie ligatures, use of chain elastics, use of lingual retention wires 20 and related features and materials utilized to manipulate the patient's teeth. The arch wires 504 may include straight, shaped in a preset arch for, may be both shaped in an arch form and curved in a 3D dimension or may be otherwise configured. The orthopedic hardware may include luggage loops with button or elastic styles, intra-arch elastics with various configuration, molar tube brackets 16 with slots 16a, lingual brackets 22 that engage arch wires 504 or the lingual wires 20, palate expanders 30, the lingual retention wires 20 and related hardware. The analysis and prediction module 307, 407 may also be able to recommend and predict outcomes of the patient 304, 404 being treated based on historical dental records of a plurality of additional patients by comparing features of the first patient 304, 404 to historical features and information of the plurality of additional patients. The preferred systems 300, 400 and methods 100, 200 are utilized with fixed appliances, i.e. brackets 503, wires 504, and related fixed appliance hardware. Between the transmitting of the stored images and measuring outcomes based on the prescribed treatment, the preferred systems 300, 400 preferably use computer/machine learning to predict outcomes based on the prescribed treatment. The predicted outcomes can be conducted on a treatment by treatment basis or multiple times for the same or a similar patient during the course of treatment, such that incremental and overall outcomes and times are predicted by the system 300, 400 to provide a patient 304, 404 with typical treatment timelines and outcomes. The predicted outcomes may also produce a range of outcomes based on a patient's 304, 404 compliance with treatment recommendations, physical characteristics of the patient 304, 404 and other variables that may impact outcomes.

The preferred brackets 503 may be comprised of passive self-ligating brackets with a Roth or an MBT prescription and a preferable slot size of between eighteen thousandths to twenty-two thousands inches (0.018-0.022"). Hooks or "posts" may be designed into the brackets 503 on either the mesial or distal side of the tooth and the hooks may be used for any tooth that is preferably not a central or lateral incisor. The hooks preferably extend outwardly (gingival) from the bracket. The hooks are preferably used to attach elastics at different times during treatment.

Referring to FIGS. 1-5F and 7, for a distal tooth or in some cases the two most distal teeth in each quadrant of the patient's mouth a molar tube bracket 16 is preferably attached to the patient's tooth. The molar tube brackets 16, rather than engage the arch wire 504, are preferably comprised of brackets 503 with a tube 16a into which the arch wire 504 is placed. The most distal tooth or teeth may, therefore, be bonded with the molar tube style bracket 16. The molar tube brackets 16 are typically distinct from other brackets in that the arch wire 504 is placed into the molar tube 16*a* through a slot in the bracket 503. The preferred molar tube bracket 16 is comprised of a Rickets prescription, bondable directly to the tooth with a mesial-distal length of approximately three and six tenths millimeters (3.6 mm) or similar sizes to the tooth and a hook or "post" 16*b* that extends distally. While the preferred method of attaching the molar tube bracket 16 utilizes the direct bonding method, molar tube brackets 16 that are attached to the tooth via a band that fits over the circumference of the tooth are sometimes used, particularly if the tooth in question is a replacement tooth made of a non-natural material. The molar tube brackets 16 also preferably have a relatively low profile for patient comfort, a criss-cross permanent guide 18 comprised of marks on a facial surface that assist in bonding and positioning, the cross-cross permanent guide 18 may be color-enhanced such as having green or red along one of the criss-crosses for appropriate positioning, an entrance to the molar tube 16*a* may be funneled to help guide the wire into the molar tube 16*a* and the hook 16*b* may be comprised of a malleable ball hook that enhances patient comfort and avoids gingival impingement.

Referring to FIGS. 1-10, the brackets 503 and wires may also be configured for mounting to the lingual side, such as lingual brackets 22 and wires 20 of the teeth rather than the front surface of the teeth. The concepts of placing the brackets 503, and using the same toolbox of wires and other techniques is largely the same. The lingual-style braces, including the lingual brackets 22 and wires 20, may also be modeled and configured for use with the preferred systems 300, 400. The lingual braces 20, 22 are a preferably fixed orthodontic treatment appliances which involve attaching the orthodontic brackets 22 on the inner sides of the teeth. Lingual retention is preferably used to prevent the teeth from moving back to their original position after orthodontic treatment is completed, although is not so limited. This lingual retention method may utilize a bonded lingual retainer appliance 24, such as a braided stainless steel wire 24, that connects to the lingual side of the front teeth. Composite resin or other adhesive or attachment mechanisms 26 or methods may be used to adhere the appliance 24 to the teeth The preferred systems 300, 400 are configured to store and measure dental imaging records via a computer modeling system and aggregating and cross-referencing clinical results across a statistically significant number of cases. At least one of the preferred goals of such analysis is to analyze the efficacy of specific procedures and how they relate to movements of the patient's teeth. Measuring individual and overall tooth movements (in any direction) during an orthodontic treatment based on treatment protocols and time between images taken is beneficial for patient 304, 404 and practitioner (consultant orthodontist 305, 405 and/or general dentist 306, 406) planning and pricing strategies. The analysis and prediction modules 307, 407 of the preferred systems 300, 400 are preferably included in the network 301, 401, which has access to the servers 302, 402, including the patient digital dental record, prior to initiation of treatment and during treatment such that the systems 300, 400 are able to compare and contrast similar patient cases for prediction and modeling purposes.

The preferred systems 300, 400 are able to use artificial intelligence and machine learning to create computer models that are capable of prescribing orthodontic treatment. For example, the artificial intelligence and machine learning component of the preferred systems 300, 400 may be operated on a macro treatment protocol or a visit-by-visit basis. Past experience of the systems 300, 400, therefore, can enable the preferred systems 300, 400 to become a virtual consultant orthodontist 305, 405 by providing a treatment protocol based on known past treatments and results, particularly when comparing potential treatments to similarly situated patients. The systems 300, 400 are able to design and develop treatments based on a combination of results from actual patients and simulated patients, results from all actual patients and historical results or results from all simulated patients and simulated results. The preferred systems 300, 400 are configured to utilize images of the patient's 304, 404's arches that are taken by a general practice ("GP") dentist, the patient or otherwise collected to create a three-dimensional ("3D") model of the patient's arches for development of an orthodontic treatment plan and selection or creation of orthodontic hardware for application to the patient's teeth and arches. The images may be collected directly by a scanner, camera or other imaging device and may be collected directly by the patient, dental professionals, technicians or otherwise, such as by utilizing mirrors or lenses to facilitate capture of the images, such as for maxillary or mandibular occlusal image capture. The 3D model may be created by an indirect bonding ("IDB") laboratory, by the preferred systems 300, 400, by the GP dentist, by the consulting orthodontist or otherwise for planning and modelling purposes. The 3D model is preferably utilized to develop customized IDB bonding trays for the patients, but the systems 300, 400 and methods are not so limited and the orthodontic hardware may be otherwise designed and applied, such as by placing braces by hand by established protocols, based on the consulting orthodontist's recommendation, which is communicated to the GP dentist, a physical custom made template that can be used to position the orthodontic hardware by hand placement, a template that enables the GP dentist to mark the teeth, which guides hand placement of the orthodontic hardware or other similar systems and methods.

The preferred systems 300, 400 utilize the analysis and prediction or artificial intelligence module 307, 407 and machine learning to effectively predict the impact of prescribed treatments on the patient's 304, 404 jaw and teeth or arches and an expected timeframe for changes, as well as a range of outcomes. The systems 300, 400 of the preferred embodiments are able to understand, chart, store and measure the various physical properties of the patient's 304, 404 mouth in order to predict outcomes and develop treatment strategies based on past treatment strategies and results. The systems 300, 400 of the preferred inventions contemplate observing, measuring and calculating one or more of the a) size and shape of the mandibular and maxillary bones of the patient 304, 404, b) the distances between the patient's 304, 404 teeth, c) the tooth root structure (length, shape and angle of the roots) of the patient 304, 404, d) the dentition (number of teeth, size of teeth, baby teeth present, etc.) of the patient 304, 404, e) age of the patient 304, 404, f) periodontal issues of the patient 304, 404, g) the profile of the patient's 304, 404 face including the distance between nose and chin, h) the position of a tooth relative to the gum line, i) the size and shape of the patient's 304, 404 teeth and j) any other oral cavity properties that are similar or related to these categories or that are able to assist in the treatment and prediction of treatment outcomes.

The described preferred features and measurements of the systems 300, 400 can be derived by one or more of the various input methods and systems. The input methods and systems are preferably comprised of a portion of a first communication device 303, 403 and may include cameras, intraoral photographs, intraoral scans, x-rays, three-dimensional imaging such as a cone-beam computerized tomography ("CBCT") scanner, cat scan or magnetic resonance imaging ("MRI") or other related techniques or methods that are able to determine the preferred features and measurements of the patient 304, 404 and operate within the preferred system 300, 400, as is described herein. The first communication device 303, 403 may include a camera comprised of a digital camera with a wireless connection to the Internet using Bluetooth or Wi-Fi to facilitate transmittal of images to the systems 300, 400. The first communication device 303, 403 or systems 300, 400 may also be in communication with a personal mobile device or tablet of the patient for collection and transmittal of patient information for the patient's dental or health records, including images of the patient's arches. The input methods, features and measurements can be conducted or taken at the general dentist 306, 406, a third party location or nearly anywhere where the methods, features and measurements can be transmitted to the networks 301, 401 by the first communication device 303, 403 and subsequently to the server 302, 402, preferably by also utilizing the communication devices 303, 403.

Particular appointments of the patient 304, 404 at a preferred treatment center or a location of the general dentist 306, 406 may utilize various treatment protocols, which may include using different gauge orthodontic wires 504, including arch wires 504, inter-arch elastics 505, common ties 506 and ligatures 507, which apply distinct forces on teeth during different phases of treatment. In one embodiment, the present invention includes wires 504 with gauges ranging from twenty-eight to twenty-two (28-22) or twelve thousandths to twenty-five thousandths of an inch (0.012-0.025"), preferably constructed of nitinol, which are preferably round or rectangular, but also other metal wires, including stainless steel may be utilized. The gauges of the wires 504 may more preferably range from twenty-seven to twenty-five (27-25) or fourteen thousandths to eighteen thousandths of an inch (0.014-0.018"). Following collection of images of the patient's 304, 404's arches, preferably including the jaw, mouth and teeth with the first communication device 307, 407, storing the images, transmittal of the images to the network 301, 401, review of the images and the patient's 304, 404 historical dental records by the consultant orthodontist 305, 405, and a recommendation from the consultant orthodontist 305, 405, or the automatic treatment strategy from the systems 300, 400, the treatment protocol may suggest using hardware 503, 504, 506, 507, such as palate expanders 30, self-ligating orthodontic brackets or traditional brackets 503 held in place by ligatures 507, using elastics 50 in different configurations such as "Class II, Class III, Boxes-Verticals, Cross bites and Anterior open bite" to manipulate tooth movements and/or to affect the patient's 304, 404 bite, using the lingual buttons 14 in combinations with elastics 50 to change the position of the tooth, luggage loops to effect—roll, pitch and or yawl, using coiled springs to create space between teeth, using flexible "power chains" to close spaces between teeth, using common ties 506 to stabilize tooth movements, using indirect bonding techniques to place brackets 503 on the teeth, using crimp stops to minimize shifting or orthodontic wires between the brackets 503, using lingual wires 20 bonded directly to teeth to minimize shifting of teeth during and post treatment, using palate expanders 30 to expand bone structure, using 3D modeling techniques to determine and suggest optimal bracket 503 location on individual teeth and utilizing additional hardware or structures to manipulate the patient's jaw and teeth, as would be apparent to one having ordinary skill in the art based on the present disclosure. The communication between the general dentist 306, 406 and the consultant orthodontist 305, 405 preferably is conducted by the general dentist 306, 406 initiating communication with the consultant orthodontist, 305, 405 with the first communication device 303, which may be comprised of multiple communication devices 303. The first communication device 303 sends information to the network 301 and the consultant orthodontist 305, 405. The communication may be initiated automatically when the images are uploaded from the general dentist 306, 406 through the first communication device 303 to the network 301 or manually by the general dentist 306, 406 (including their staff, a technician, hygienist or other employee). The first communication device 303 sends a message to the network 301 indicating that the general dentist 306, 406 is ready for a consult from the consultant orthodontist 305, 405 on the particular case or a series of cases that the general dentist 306, 406 is arranging, typically with the patient in the general dentist's 306, 406 office. The consultant orthodontist 305, 405 then replies or initiates a separate communication through a second communication device 308, 408 to the general dentist 305, 405 for the consultation regarding the specific patient 304, 404 or series of patients. The systems 300, 400, preferably including the analysis and prediction, artificial intelligence or machine learning module 307, 407, may determine expected outcomes and provide an indication of patient compliance with treatment protocols, such as patient 304, 404 compliance with wearing particular elastics 50 or retainers between appointments based on comparing expected movement to actual movement.

The preferred invention contemplates that to optimize the efficacy of treatment, the use, timing, combination and sequence of any of the above treatment methods should be considered. The preferred invention contemplates that decisions regarding treatment methods prescribed and used during any particular patient appointment would be made based on an assessment of the imaging and tooth positions recorded at the time of that appointment.

Using historical results from completed cases of actual patient 304, 404 and/or simulated cases stored in the databases in the server 302, 402, the network 301, 401 is prompted to compare cases that are active and would facilitate a method to monitor treatment progress in real time. This allows the general dentists 306, 406 to: a) identify cases whereby progress is not as expected and b) review possible reasons, which may include; patient 304, 404 non-compliance with elastics 50, poor oral hygiene, patient 304, 404 retainer usage issues, patient 304, 404 health or clinical execution errors. Such a monitoring system incorporated into the networks 301, 401 is preferred for general dentists 306, 406 and their patients. General dentists 306, 406 could then share expected result vs. the actual results with the patient 304, 404 and discuss reasons why the results are not as expected, such as failure of the patient 304, 404 to comply with treatment recommendations. The consultant orthodontist 305, 405 and general dentist 306, 406 also preferably provide treatment options and immediate suggestions based on each individual patient visit, although the general dentist 306, 406 may alternatively follow a treatment plan that is developed at an initial appointment, particularly if expected progress of the patient 304, 404 matches the expectations of the treatment plan. The preferred appointment by appointment treatment strategy facilitates individual and custom treatment for the patient 304, 404 that adapts to the individual patient 304, 404, such as a patient 304, 404 who progresses more quickly than predicted and may complete their treatment comparatively early or a patient 304, 404 who progresses comparatively slowly and may have their treatment extended to accommodate completion of the treatment.

The preferred systems 300, 400 and methods 100, 200 are typically utilized, but are not so limited, to begin treatment no earlier than nine (9) years old such that the arches, including the jaw and teeth of the patient 304, 404, are relatively mature and appropriate for manipulation. The system 300, 400 and method 100, 200 recommends that every patient 304, 404 over twenty-five (25) years old should have a periodontal exam prior to participation in the program. The preferred systems 300, 400 and methods 100, 200 are generally utilized with no or a limited number of functional appliances, including Herbst appliances. In the preferred embodiments, a pallet expander is generally preferred for use in bilateral cross bites.

The exemplary preferred systems 300, 400 and methods 100, 200 may include indirect bonding of an eighteen thousandths to a twenty-two thousands inch (0.018-0.022") self-ligating bracket and fourteen thousandths (0.014) nitinol wire 504 or sixteen thousandths (0.016) nitinol wire 504 with buttons and or rotations prescribed, if needed. If spaces need to be closed, it is preferred that the general dentist 306, 406 use power chain elastics. The preferred systems 300, 400 then may utilize seventeen thousandths by twenty-five thousandths (0.017×0.025) nitinol wires 504 with common ties 506 and/or elastics 507 if needed. The systems 300, 400 of the preferred methods 100, 200 then utilize a finishing wire 504, such as eighteen thousandths (0.018) stainless steel wire 504 with common ties 506 and any additional finishing elastics 507. In the preferred systems 300, 400 and methods 100, 200, elastics 507 are preferably Class II, Class III, boxes-verticals and cross bites-all elephants, three-sixteenths inch (3/16"), preferably three and one-half ounce (3.5 oz.) or one quarter inch (¼"), preferably three and one-half ounce (3.5 oz.) elastics, such as anterior open bite and related equipment. If spaces need to be opened at any time during treatment the preferred systems 300, 400 preferably utilize coil springs. In order to keep the wires 504 from shifting within the brackets 503, the preferred systems 300, 400 preferably utilize crimp stops, preferably not between front teeth for aesthetic purposes. The molar tube bracket 16 is preferably comprised of a standard bracket 503, not necessarily an EasyClip or a Smart Clip, but may be comprised of self-ligating brackets, such as EasyClips or Smart Clips. An arch wire 504 for mandibular and maxillary are different product item numbers and may be utilized with the preferred systems 300, 400 and methods 100, 200.

In a preferred method utilizing the systems 300, 400, the first patient 304, 404 meets with the general dentist 306, 406 at an initial appointment and the dental records of the first patient 304, 404 are communicated to the network 301, 401 and the server 302, 402, potentially through the first communication device 303, 403 or a separate communication device. The consultant orthodontist 305, 405 reviews the first dental records on the first communication device 303, 403 and the general dentist 306, 406 takes images of the first patient's 304, 404 arches utilizing a scanner, such as a digital camera, a 3D scanner, an intraoral scanner, a video recorder, and other imaging equipment. The intraoral scanner may be placed inside the patient's mouth to capture 3D images of the patient's teeth and arches, such as a Prime Scan by Dentsply. The patient's teeth and arches may also be modeled by traditional physical impressions that may be maintained by the GP dentist for subsequent scanning, at the dentist's convenience. The traditional physical impression may also be converted into a physical or digital model of the patient's teeth and arches. The scanner may also be comprised of a radiograph imaging device having features such as a panoramic x-ray machine, computer tomography ("CT") scanner, CBCT scanner that is able to provide 3D dimensional imaging of the patient's arches, jaw, facial bone structure, teeth and related structures and related imaging devices.

The arches are preferably comprised of at least the patient 304, 404's teeth and may also include bone and soft tissue 501 adjacent to the patient's 304, 404 mouth, such as gums, cheeks, lips and related anatomical structures that are relevant to the consultant orthodontist's analysis of the patient 304, 404 and preparation of the treatment plan. The images may include mandibular occlusal, maxillary occlusal, right buccal, left buccal, intra-oral center and related images of the patient's arches. The images are communicated by the general dentist 305, 405 to the network 301, 401 utilizing the first communication devices 303, 403 and the images are routed to and stored in the first dental records in the network 301, 401, preferably the server 302, 402. The upload of the images automatically indicates or a separate message from the general dentist 306, 406 and staff to the consultant orthodontist 305, 405 indicates that the general dentist 306, 406 is prepared to a consult with the consultant orthodontist 305, 405. The consultant orthodontist 305, 405 reviews the first dental records, including the images utilizing the second communication device 308, 408. The consultant orthodontist 305, 405 communicates with the general dentist 305, 405 for a consultation regarding the first patient 304, 404 to address malocclusions using braces, preferably through the network 301, 401 utilizing the first and second communication devices 303, 403, 308, 408, respectively. The consultant orthodontist 305, 405, potentially with input from the general dentist 306, 406, develops a treatment plan related to the diagnosis and treatment plan of the first patient 304, 404 based on the review of the first dental records, including the images uploaded during this initial consult. The consultant orthodontist 305, 405 preferably conducts live consultation with the general dentist 306, 406 and potentially the first patient 304, 404 to communicate a treatment plan. The live consultation may utilize conferencing systems and protocols while the patient 304, 404 is with the general dentist 306, 406.

Based on the suggested treatment plan, the consultant orthodontist 305, 405 directs fabrication of one or more transfer trays based on the images uploaded during the initial first patient 304, 404 appointment and the first dental records. The transfer trays and braces, preferably self-ligating braces, are delivered to the general dentist 306, 406 and the general dentist 306, 406 schedules a subsequent or second appointment with the first patient 304, 404. The general dentist 306, 406 removably and adjustably affixes the braces to the first patient 304, 404 at the second appointment, collects images of the first patient 304, 404's arches before, and potentially after, affixing the braces to the first patient 304, 404 utilizing the first communication device 303, 403, communicates the images to the network 301, 401 with the first communication device 303, 402, the images are stored in the server 302, 402 in the first dental records and the consultant orthodontist 305, 405 reviews the first dental records utilizing the second communication device 308, 408, including the images from the second appointment. The general dentist 306, 406, based automatically on the uploading of the images to the first patient 304, 404 or by a separate communication, indicates to the consultant orthodontist 305, 405 that a consultation is desired. The consultant orthodontist 305, 405 responds or initiates a separate communication to the general dentist 306, 406 for a consultation regarding the first patient 304, 404 and, potentially, additional patients that are preferably at the general dentist's 306, 406 office, and provides consultation and treatment strategy for the first patient 304, 404 based on the first dental records, which were updated with the images from the current appointment. The consultation with the consultant orthodontist 305, 405 may be live and include video review of the braces and the first patient 304, 404's arches or consultation while the braces are placed on the first patient 304, 404, preferably through the network 301, 401.

A subsequent follow-up appointment or an appointment following an initial or interim consultation is preferably scheduled with the first patient 304, 404. The first patient 304, 404 returns to the general dentist 306, 406, images of the arches are secured with the first communication device 303, 403, the images from the appointment are communicated to the network 301, 401 with the first communication device 303, 403 and stored in the server 302, 402 and the consultant orthodontist 305, 405 reviews the first dental records with the second communication device 308, 408. The images may also be taken and transmitted to the server 302, 402 by the patient prior to or in place of a physical visit to the offices of the general dentist 306, 406. The general dentist 306, 406, based automatically on the upload of the third images or based on a separate communication, communicates a desire for a consultation with the consultant orthodontist 305, 405 for the first patient 304, 404 and, potentially, with additional patients that are at the general dentist's 306, 406 office, preferably through the network 301, 401. The consultant orthodontist 305, 405 responds to the general dentist 306, 406 to conduct a consultation based on the first dental records, including the updated images from the third appointment and provides a treatment plan and strategy based on the current status of the first patient's 304, 404 arches. The treatment strategy and plan, therefore, is preferably developed based on each appointment and the condition of the patient's 304, 404 arches at each appointment, in addition, the plan may follow a treatment plan and strategy that is developed during the initial or first appointment without significant input from the consultant orthodontist 305, 405 during subsequent appointments, particularly during treatment where the patient's 304, 404 progress generally follows the original treatment plan and strategy. Each treatment strategy and plan is preferably an optimal treatment strategy and plan based on the most updated information regarding the first dental records, including the updated images collected during each appointment as the first patient 304, 404 returns for appointments. The treatment and communications continue until the consultant orthodontist 305, 405 and the general dentist 306, 406 determine that the treatment is complete.

The preferred systems 300, 400 are configured for providing orthodontic treatment to the patient 304, 404 wherein the general dentist 306, 406 receives direction, including at least one of general and specific instructions from the consultant orthodontist 305, 405. The system 300, 400 includes the network 301, 401, which is configured to assign the consultant orthodontist 305, 405 to the general dentist 306, 406. The consultant orthodontist 305, 405 is located remote from the general dentist 306, 406. In the preferred embodiments, the network 301, 401 receives physical properties of the first patient's mouth during treatment from the first communication device 303, 403. The physical properties of the first patient's mouth are preferably compared to the first patient's dental record and the plurality of additional patient's historical dental records to predict additional outcomes for the first patient. The physical properties of the first patient's mouth may include information about the patient's arches, such as size and shape of a mandibular bone, size and shape of maxillary bones, distances between the first patient's teeth, tooth root structure, including length and angle of the tooth root structure, dentition of the first patient's teeth, including, number of teeth, size of teeth and presence of baby teeth, the first patient's age, periodontal issues of the first patient 304, 404, profile of the first patient's face, including a distance between a nose and a chin of the first patient 304, 404, position of a tooth relative to a gum line of the first patient 304, 404 and related information about the patient's arches or other features that may assist the consultant orthodontist 305, 405 in developing the treatment plan.

The network 301, 401 also preferably includes a central server 302, 402 with a patient database storing a first dental record of a first patient 304, 404 and a plurality of additional dental records of a plurality of additional patients. The network 301, 401 also preferably includes an analysis and prediction module 307, 407 configured to utilize artificial intelligence and machine learning to predict an impact of prescribed treatments on the jaw and teeth of the first patient 304, 404, as well as to predict expected timeframes for changes to the jaw and teeth of the first patient 304, 404. The analysis and prediction module 307, 407 is also preferably configured to predict a range of outcomes for the first patient 304, 404. The network and prediction module 307, 407 is further preferably configured to access the first dental record and at least one of the plurality of additional dental records prior to initiation of treatment of the first patient 304, 404 and to compare and contrast the first dental record and the at least one of the plurality of additional dental records to predict timing and outcome for dental treatment of the first patient 304, 404. The plurality of additional dental records also preferably include at least one of, and more preferably both, dental records of actual patients and dental records of simulated patients.

The systems 300, 400 also preferably include a first communication device 303, 403 configured to provide realtime conferencing between the general dentist 306, 406 and the consultant orthodontist 305, 405.

In another aspect, the preferred systems 300, 400 are configured for providing orthodontic treatment to a patient 304, 404 wherein the general dentist 306, 406 receives direction from a consultant orthodontist 305, 405. The system 300, 400 includes an imaging device configured to capture at least one image of arches of the first patient 304, 404. Preferably, the imaging device is one of a scanner, a digital camera, a 3D scanner, an intraoral scanner, and a video recorder. The system 300, 400 also preferably includes a first communication device 303, 403 configured to control the imaging device and display the at least one image to the general dentist 306, 406 and a network 301, 401 configured to transmit the at least one image to a remote location. Displaying may comprise the at least one image being provided to the network 301, 401, which automatically develops a treatment plan based on comparison to known or historical treatments. The consultant orthodontist 305, 405 is preferably in communication with the remote location. The systems 300, 400 also preferably include a second communication device 308, 408 connected to the network 301, 401 and configured to be in mutual communication with the first communication device 303, 403. Even more preferably, the first communication device 303, 403 and the second communication device 308, 408 are configured to audio-visually communicate with one another through the network 301, 401. The second communication device 308, 408 is also preferably configured to display the at least one image transmitted by the network 301, 401 for the consultant orthodontist 305, 405.

The preferred methods 100, 200 for providing orthodontic treatment to a patient 304, 404 include a general dentist 306, 406 receiving direction from a consultant orthodontist 305, 405. The preferred methods 100, 200 also include capturing, at a first appointment, at least one image of arches of the first patient 304, 404 with an imaging device at a first location associated with the general dentist 306, 406. The imaging device is preferably one of a scanner, a digital camera, a 3D scanner, an intraoral scanner, and a video recorder, but is not so limited. The preferred methods 100, 200 also preferably include displaying the at least one image on a first communication device 303, 403 at the first location and initiating a request for a consultation with the consultant orthodontist 305, 405 by the general dentist 306, 406 with the first communication device 303, 403. The preferred methods 100, 200 further preferably include transmitting the at least one image via a network 301, 401 to a second location associated with the consultant orthodontist 305, 405 and preferably also includes automatically initiating the previously described consultation request automatically in response to transmitting the at least one image to the second location.

The preferred methods 100, 200 also preferably include displaying the at least one image on a second communication device 308, 408 at the second location. Preferably, this also includes audiovisual communication between the consultant orthodontist 305, 405 and the general dentist 306, 406 conducted between the second communication device 308, 408 and the first communication device 303, 403, although the method is not so limited. The displaying in this step may be comprised of supplying the image to the central server 301, 302, 401, 402 for analysis, manipulation and creation of a treatment plan by the central server 301, 302, 401, 402. The preferred methods 100, 200 further include the consultant orthodontist 305, 405 at the second location determining a treatment plan based on the at least one image and preferably transmitting the treatment plan from the second communication device 308, 408 through the network 301, 401 to the first communication device 303, 403. The preferred methods 100, 200 also include the general dentist 306, 406 at the first location applying dental hardware 502, 504, 506, and 507 to one or more of the teeth of the arches of the first patient 304, 404. The dental hardware 502, 504, 506, 507 may comprise braces, self-ligating braces, orthodontic wires, inter-arch elastics, ties, ligatures, and/or any other dental hardware suitable for adjusting the teeth of the patient 304, 404. As used herein, displaying the images on the first or second communication devices 303, 308, 403, 408 includes visually displaying the images for the GP dentist or the consulting orthodontist and making the images available to the central server, network or central database 301, 302, 401, 402 so that the images may be utilized to develop, create or adjust a treatment plan for the patient and select or adjust the orthopedic hardware for use during the associated procedures.

Another aspect of the preferred methods 100, 200 also includes capturing, at a second appointment, at least one additional image of the arches of the first patient 304, 404 with the imaging device at the first location, transmitting the at least one additional image to the second location, and comparing the at least one additional image to the at least one image on the second communication device 308, 408 at the second location. The consultant orthodontist 305, 405 at the second location then determines modifications to the treatment plan based on the at least one additional image and transmits the modifications to the general dentist 306, 406 at the first location. The general dentist 306, 406 then modifies or adjusts, at the first location, the dental hardware 502, 504, 506, 507.

Figure 1B:
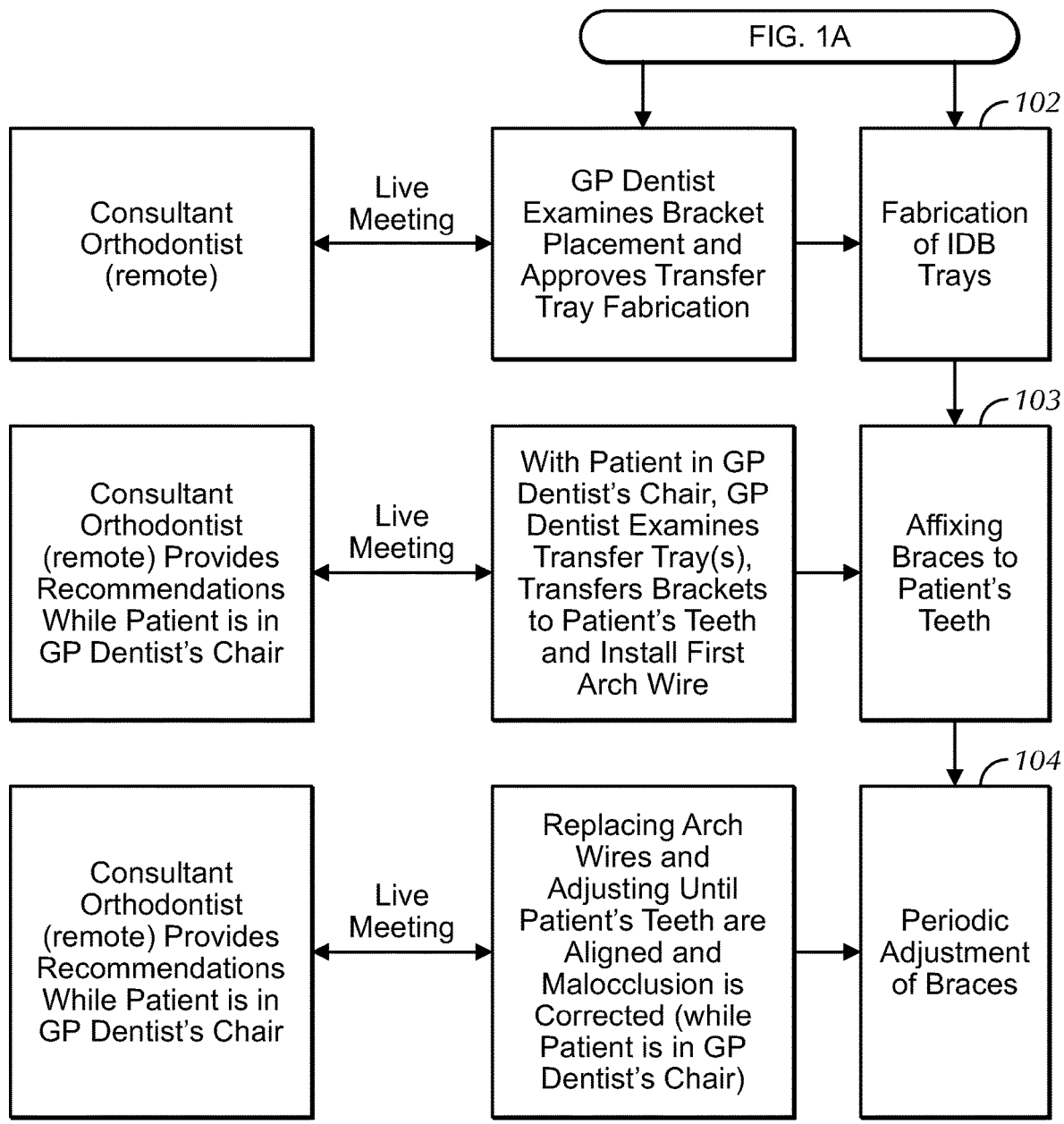
Figure 2A:
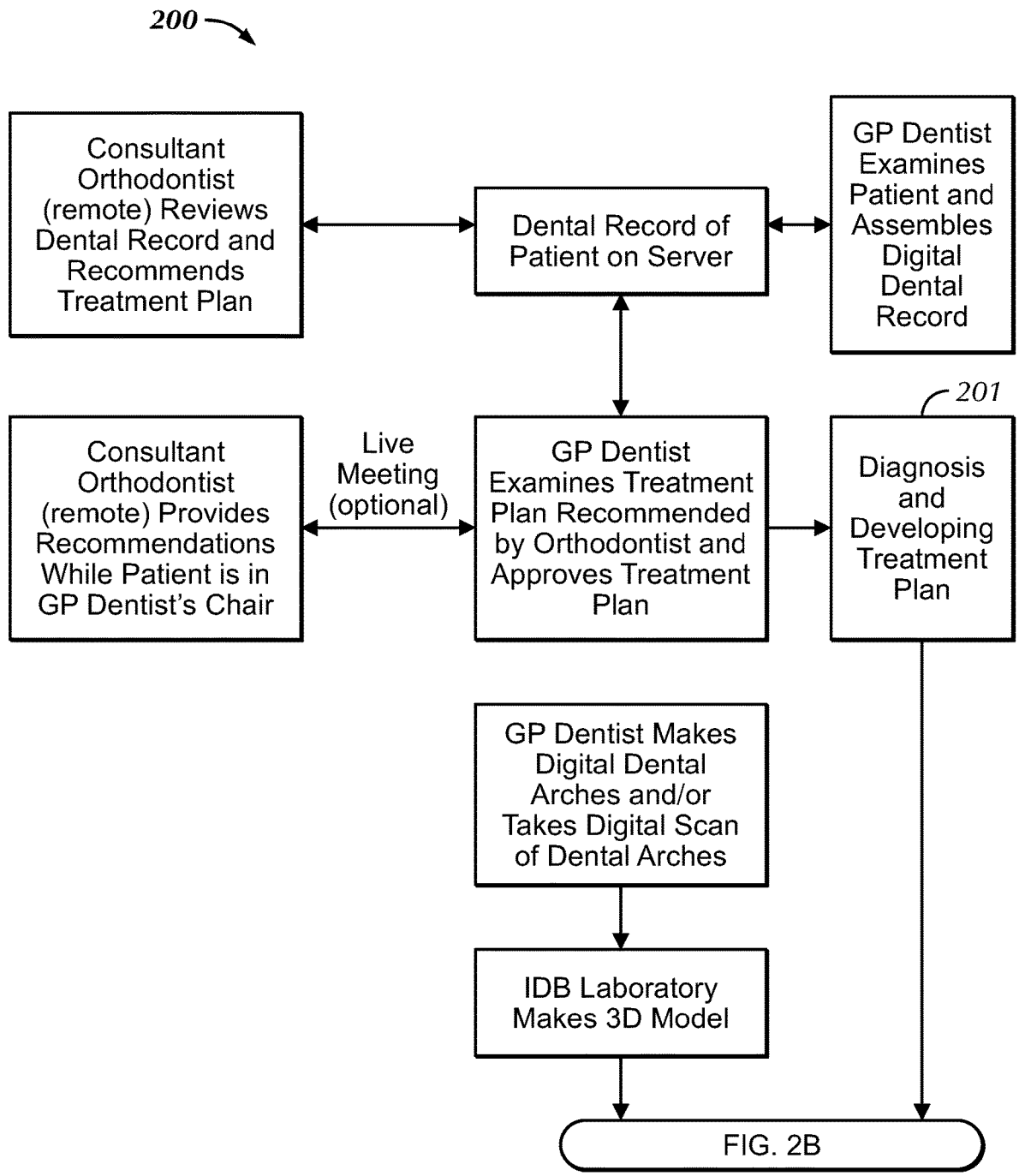
FIGS. 2A and 2B are a schematic representation of a method for providing orthodontic services to a patient in accordance with a second preferred embodiment of the present invention.
Figure 2B:
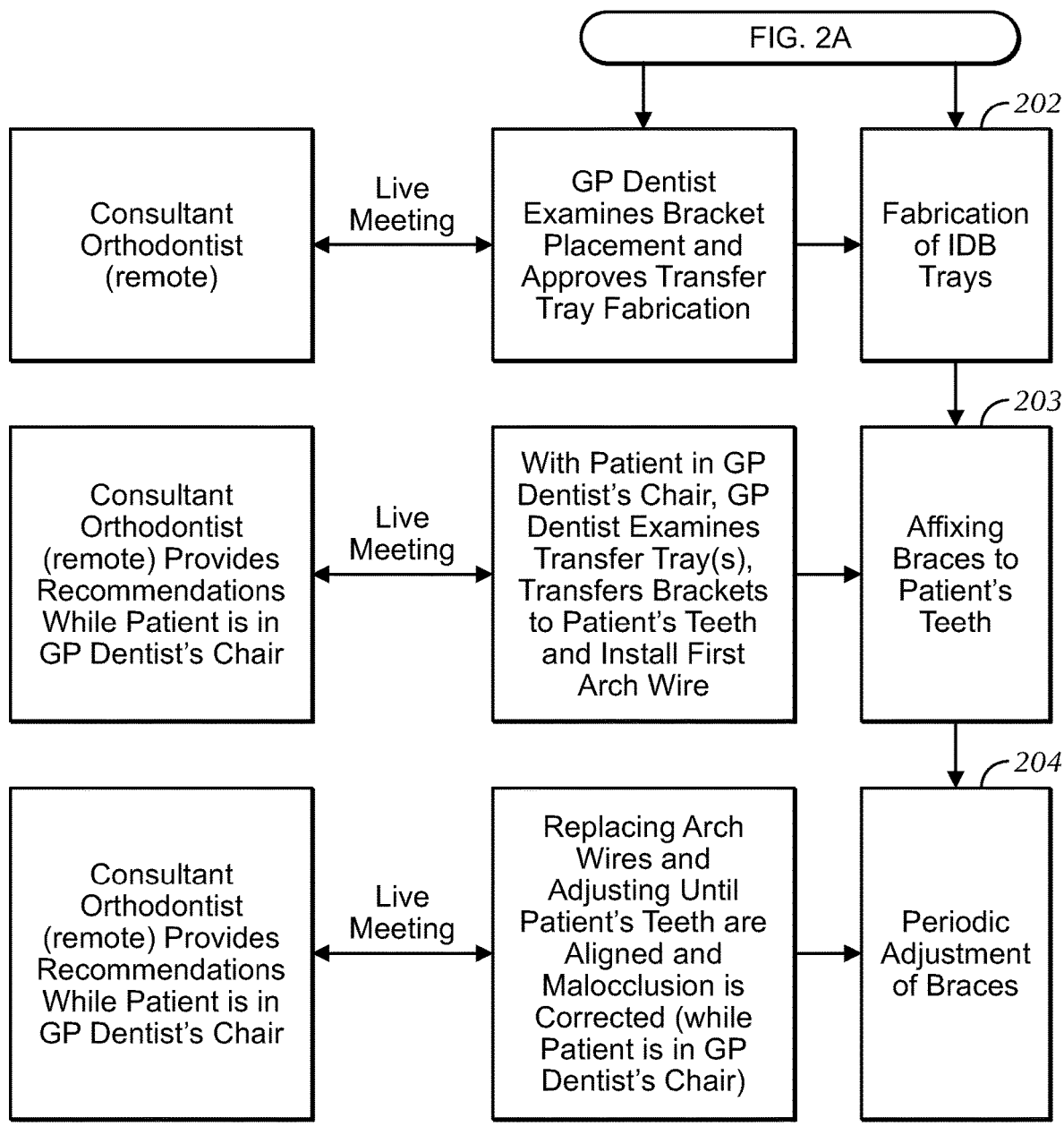
Figure 3:
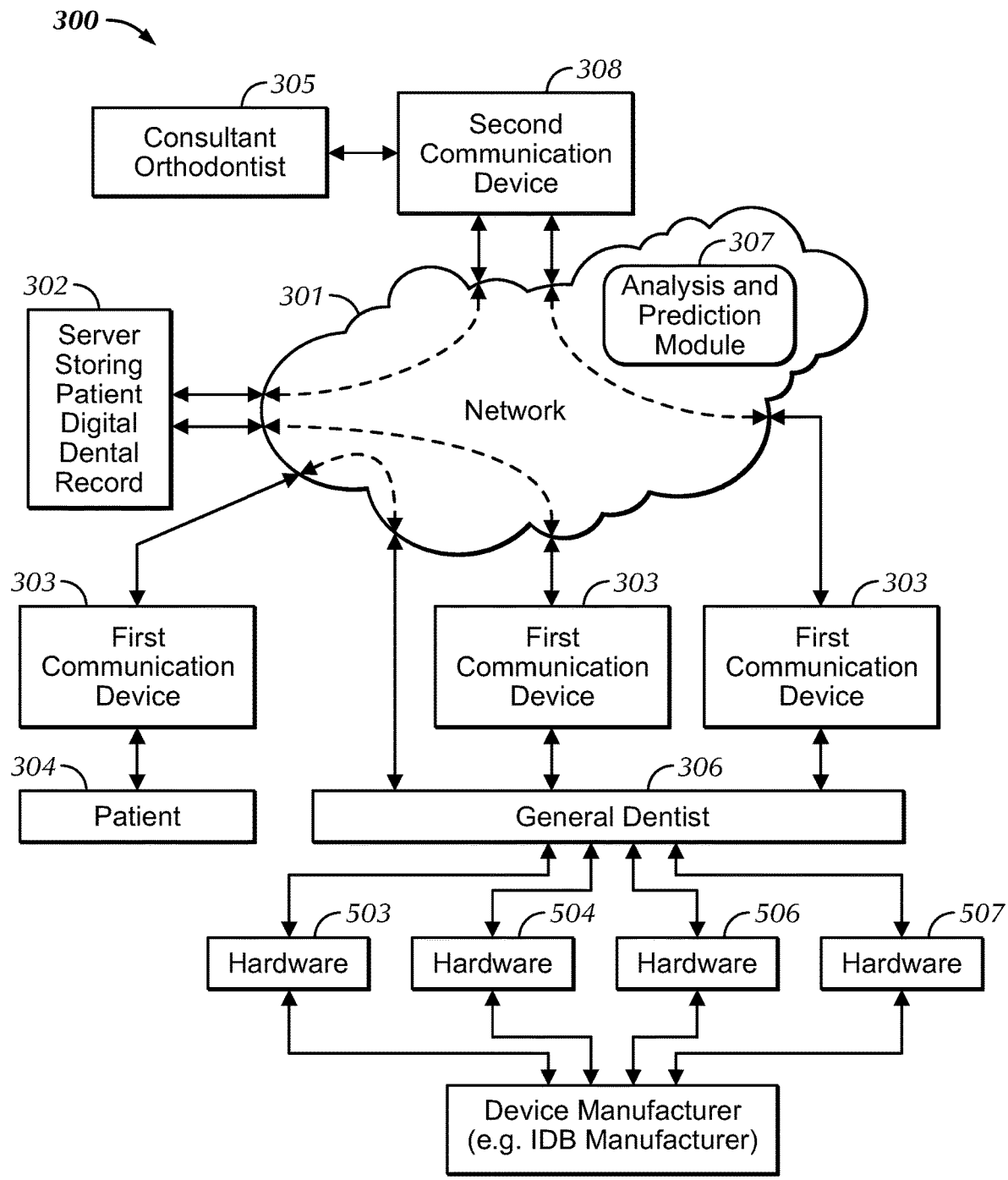
FIG. 3 is a schematic representation of a system for providing orthodontic services to a patient, which may be utilized with either of the preferred embodiments of FIGS. 1A-2B.
Figure 4:
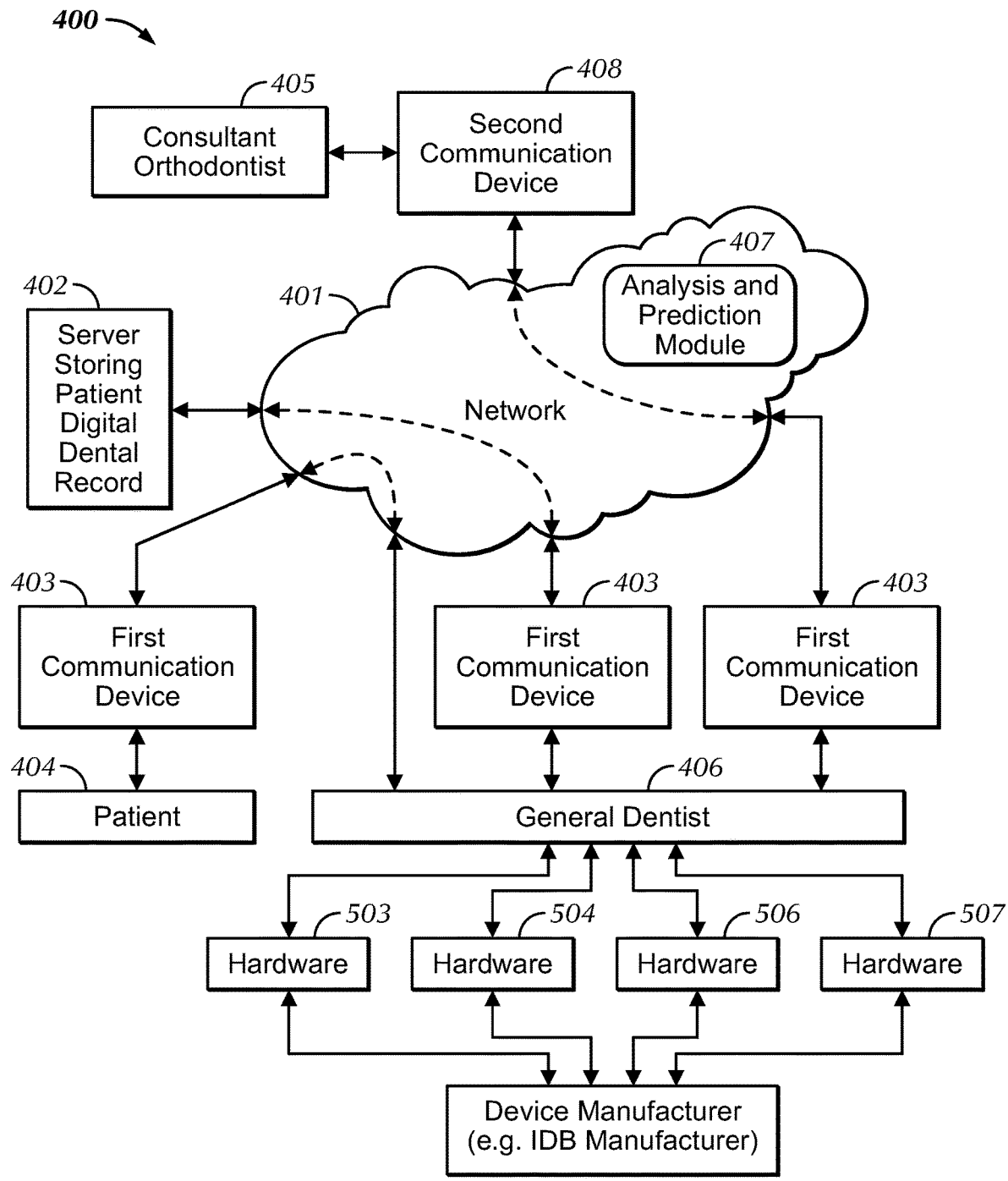
FIG. 4 is a schematic representation of a system for providing orthodontic services to a patient, which may be utilized with either of the preferred methods of FIGS. 1A-2B.
Figure 5A:
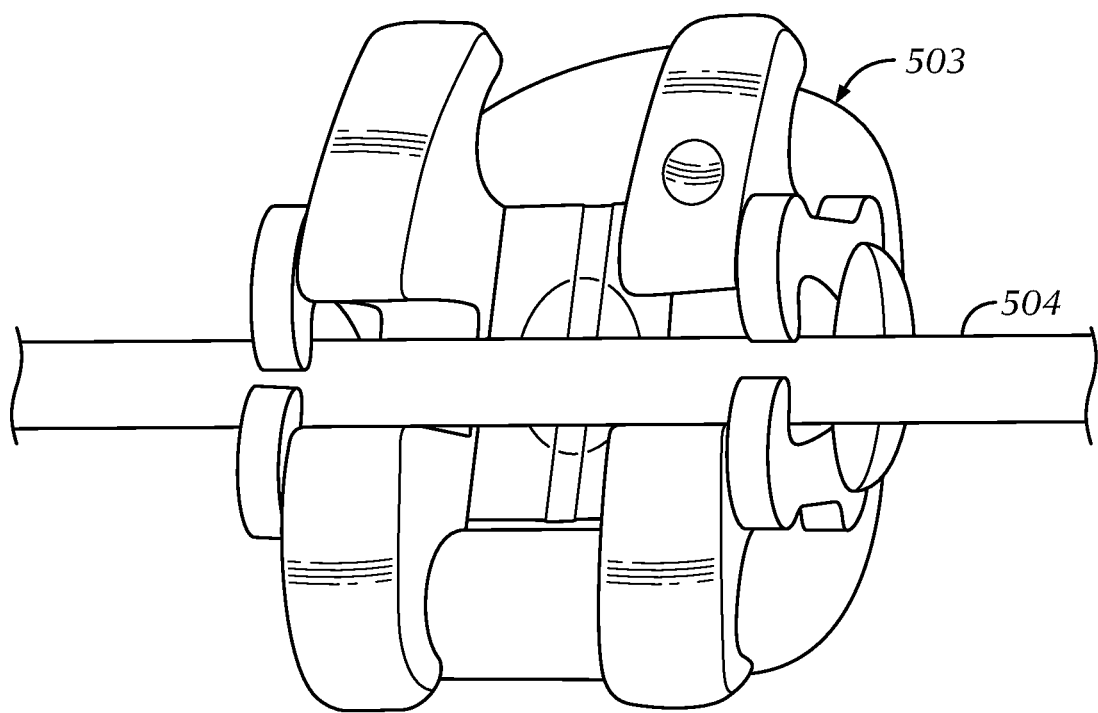
FIG. 5A is a front perspective view of an orthodontic bracket that may be utilized with any of the preferred embodiments of the invention of FIGS. 1A-4.
Figure 5B:
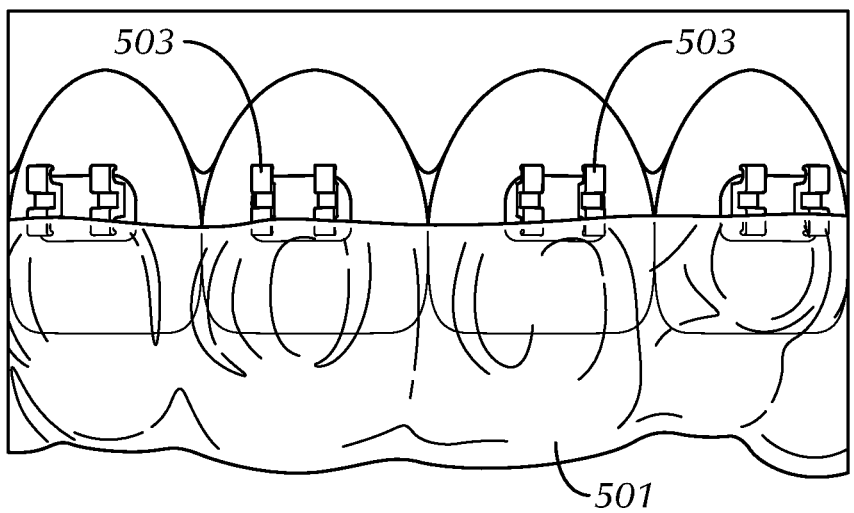
FIG. 5B is a front perspective view of a series or plurality of brackets of FIG. 5A, wherein the series or plurality of brackets are mounted to a patient's teeth.
Figure 5C:
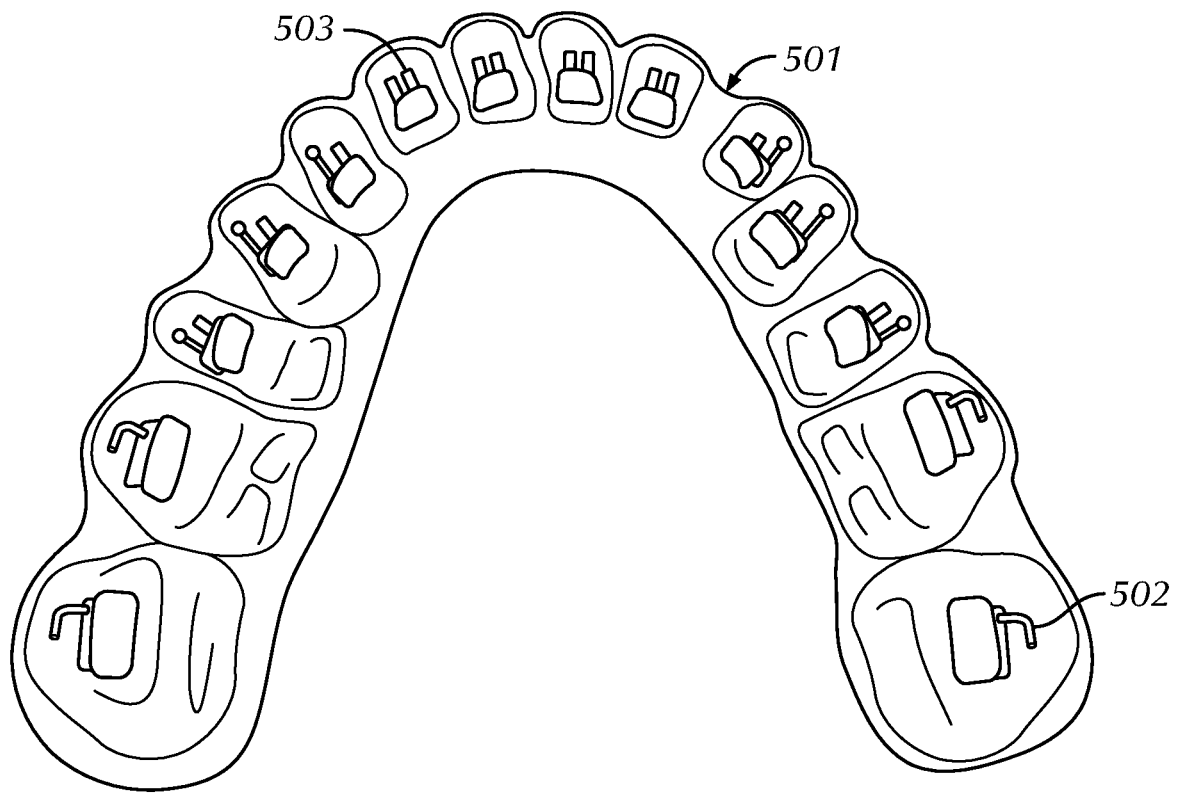
FIG. 5C is a bottom plan view of an alternative series of plurality of brackets of FIG. 5A, wherein the alternative series of plurality of brackets are mounted to the patient's teeth.
Figure 5D:
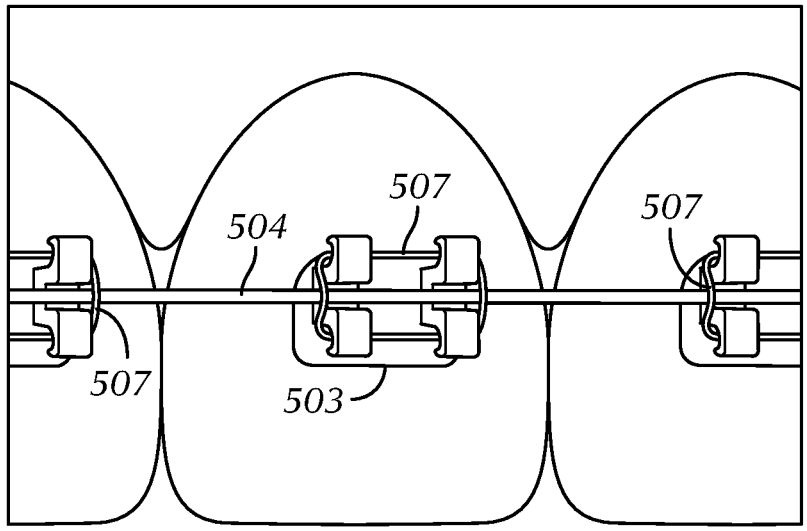
FIG. 5D is a front perspective view of orthodontic hardware that may be utilized with any of the preferred embodiments of the invention of FIGS. 1A-4.
Figure 5E:
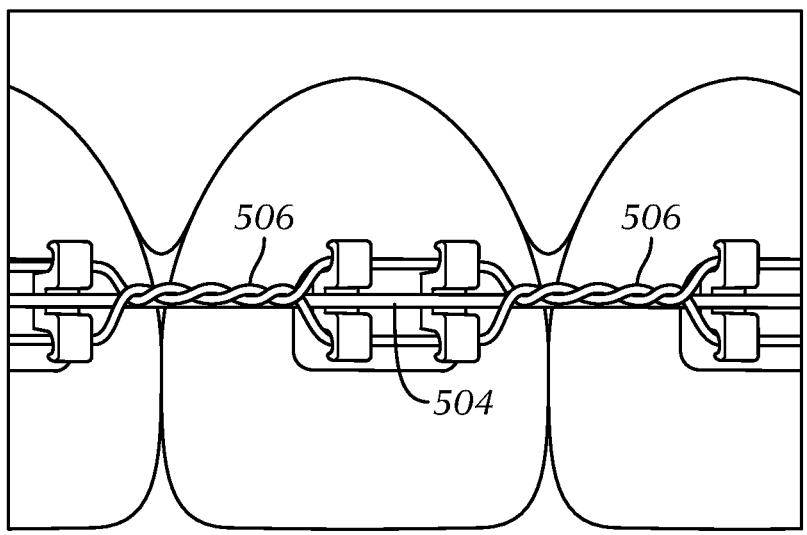
FIG. 5E is a front perspective view of alternative orthodontic hardware that may be utilized with any of the preferred embodiments of the invention of FIGS. 1A-4.
Figure 5F:
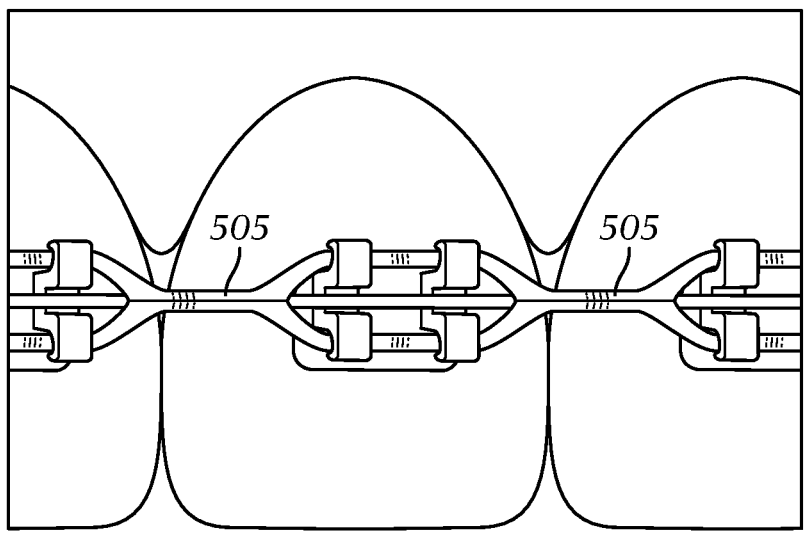
FIG. 5F is a front perspective view of further alternative orthodontic hardware that may be utilized with any of the preferred embodiments of the invention of FIGS. 1A-4.

Referring to FIGS. 1A and 1B, the preferred systems 300, 400 and methods 100, 200 for the analysis and prediction model for orthodontic treatment includes the GP dentist examining the patient and assembling the patient's digital dental record. The digital dental record may include pre-existing dental records, images taken by the patient prior to the appointment with the GP dentist, dental records from other dentists or orthodontists, medical records from other healthcare providers, information provided by the patient and other related information. The patient's digital dental record is preferably transmitted to and saved in the central server, network or central database 301, 302, 401, 402. The consultant orthodontist and GP dentist preferably have access to the patient's digital dental record through the central server, network or central database 301, 302, 401, 402. The consultant orthodontist preferably makes a diagnosis and develops a treatment plan for the patient based on the patient's digital dental record, which may change during each appointment or may be adjusted during each appointment based on changes to the patient's digital dental record. The consultant orthodontist preferably directs the treatment and use of orthopedic hardware, such as braces and related hardware, and the GP dentist employs the treatment during appointments with the patient. During routine appointments or visits, the GP dentist may replace arch wires 504 and other orthodontic hardware and adjust the hardware based on the treatment plan or direction of the consultant orthodontist. The adjustments may include various clinical procedures for aligning and fixing malocclusions of the patient. The adjustments and affixing may include use of intra-arch elastics, luggage loops, chain elastics, common tie ligatures, coil springs and related manipulation, adjusting and affixing of orthodontic hardware. The GP dentist, related personnel or the patient may make physical impressions of the teeth at various times before, during or after treatment that may be utilized for creation of 3D models or digital models. The images may also be taken or collected by the patient before an initial consultation or between consultations for transmittal to the central database 301, 302, 401, 402 such that the central database 301, 302, 401, 402 may utilize the images or the orthodontist may determine whether an initial or subsequent appointment for the patient with the general dentist or orthodontist is required, to determine if and when an appointment should be scheduled or to automatically send orthodontic hardware and instructions directly to the patient for application and use without the requirement for any direct appointment between the patient and the dental professionals.

Referring to FIGS. 1A-5, in a preferred embodiment, the systems 300, 400 utilize indirect bonding trays for performing orthodontic treatments on the patient. Each quadrant of the patient's mouth preferably has a custom fabricated, single use tray that is used to place brackets 503 in the optimal location on the teeth, as determined by the systems 300, 400. The bonding trays are not limited to including four quadrants and two quadrants may be combined into a single tray. The trays are preferably constructed of two layers, including a malleable inner layer that may be constructed of Ethylene Vinyl Acetate or other relatively malleable material that is able to take on the general size and shape of the inner layer, withstand the normal operating conditions of the inner layer and perform the functions of the inner layer and a more rigid outer layer constructed of Polyethylene Terephthalate Glycol or other more rigid material that is able to take on the general size and shape of the outer layer, withstand the normal operating conditions of the outer layer and perform the functions of the outer layer. The trays are constructed to facilitate the placement of the brackets 503 in a location determined via use of computer modeling. The trays have recesses built into them so that one or more of the brackets 503 are placed into the trays prior to putting the tray in the patient's mouth. The trays may or may not include brackets 503 for all of the patient's teeth. Once the brackets 503 are adhered to the patient's teeth using the bonding techniques described herein the trays are removed and the arch wires 504 can be attached.

A preferred method for bonding the orthodontic hardware to the patient's teeth, preferably directed by and modeled by the systems 300, 400, may include applying etch gel containing approximately thirty-five to forty-five percent (35-45%) $H_3PO_4$ phosphoric acid to each tooth with a micro brush then rinsing with water. A primer, such as Assure-Assure PLUS (brand of Primer from American Orthodontics) bonding resin, is applied to each tooth with a micro brush. Such resin can be applied to any enamel surface either wet or dry. Adhesive is preferably applied to the bracket pad surface which will bond to the tooth. The adhesive may be comprised of 3M™ Transbond™ Supreme LV Low Viscosity Light Cure Adhesive, but is not limiting. The adhesive is preferably a flowable, light cure adhesive designed for indirect bonding, but the adhesive may be otherwise designed and configured for bonding. The brackets 503 are placed on the teeth by using an indirect bonding custom fabricated trays as described above, but is also not so limited and may be otherwise placed and bonded. A curing light is preferably used to activate the adhesive curing process and the custom fabricated trays are removed from the mouth once the bracket adhesion process is complete.

Figure 6:
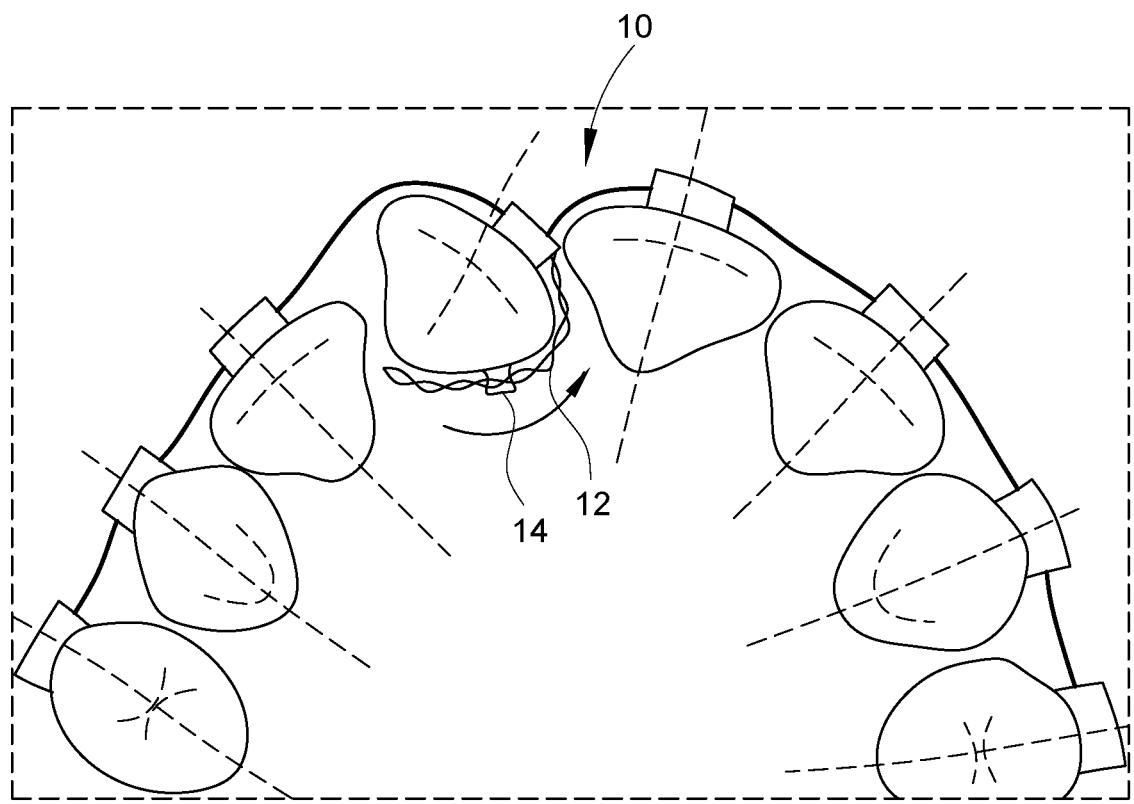
FIG. 6 is a bottom plan view of a luggage loop mounted to a patient's teeth that may be utilized with any of the preferred embodiments of the invention of FIGS. 1A-4.
Figure 7:
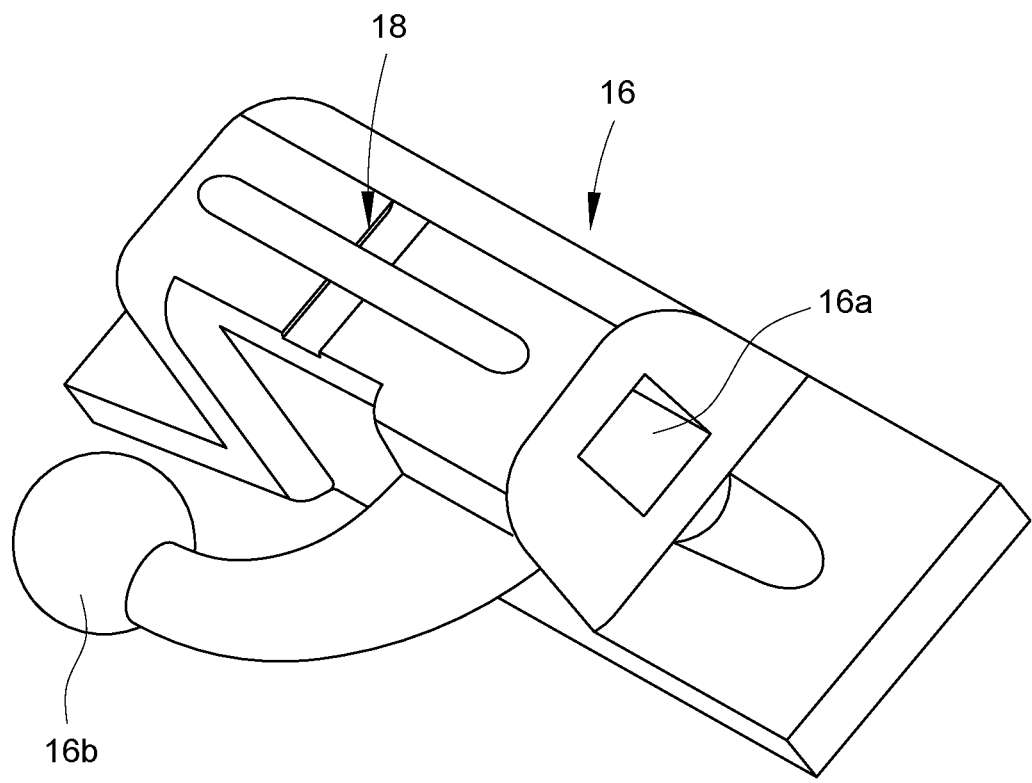
FIG. 7 is a top perspective view of a molar tube bracket that may be utilized with any of the preferred embodiments of the invention of FIGS. 1A-4.
Figure 8:
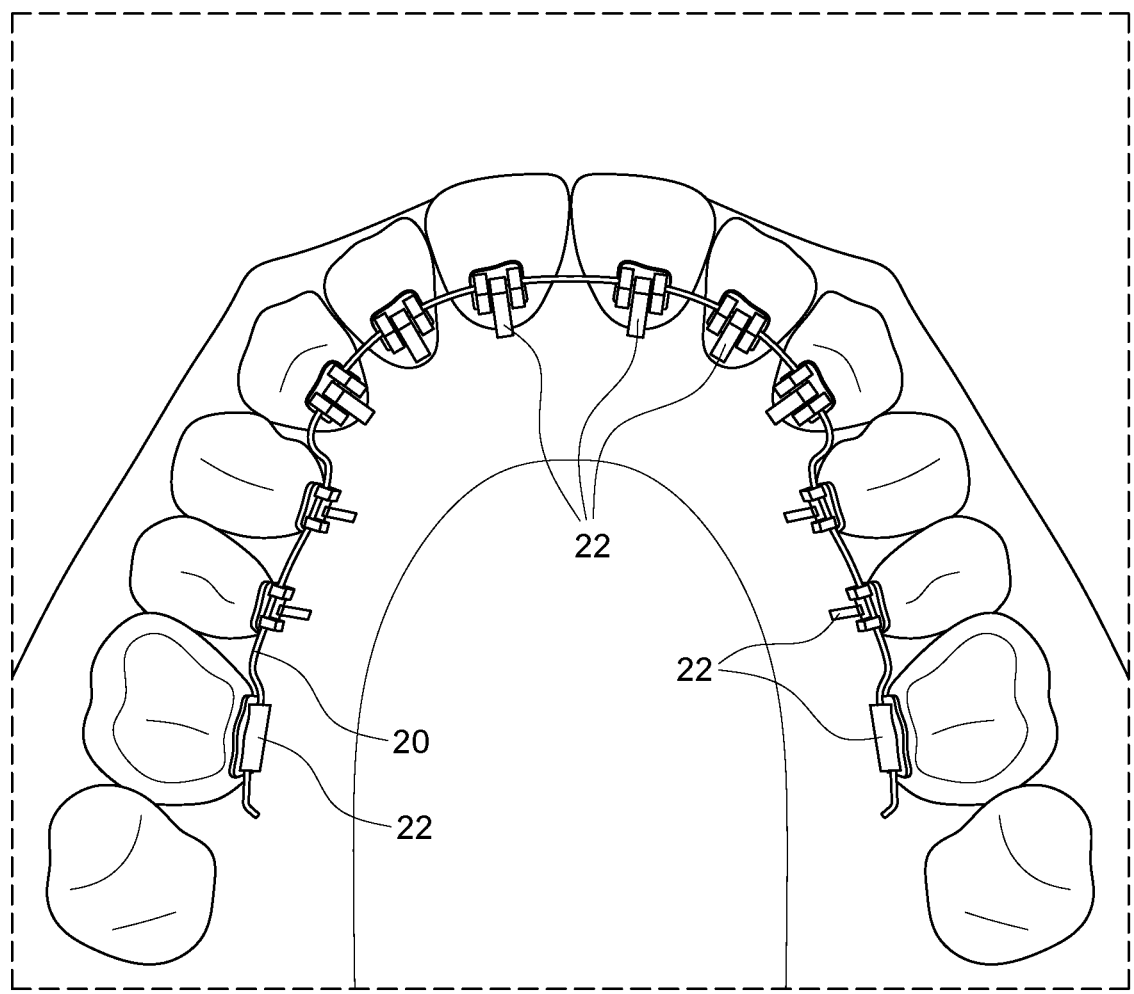
FIG. 8 is a bottom plan view of lingual wires and brackets that may be utilized with any of the preferred embodiments of the invention of FIGS. 1A-4.
Figure 9:
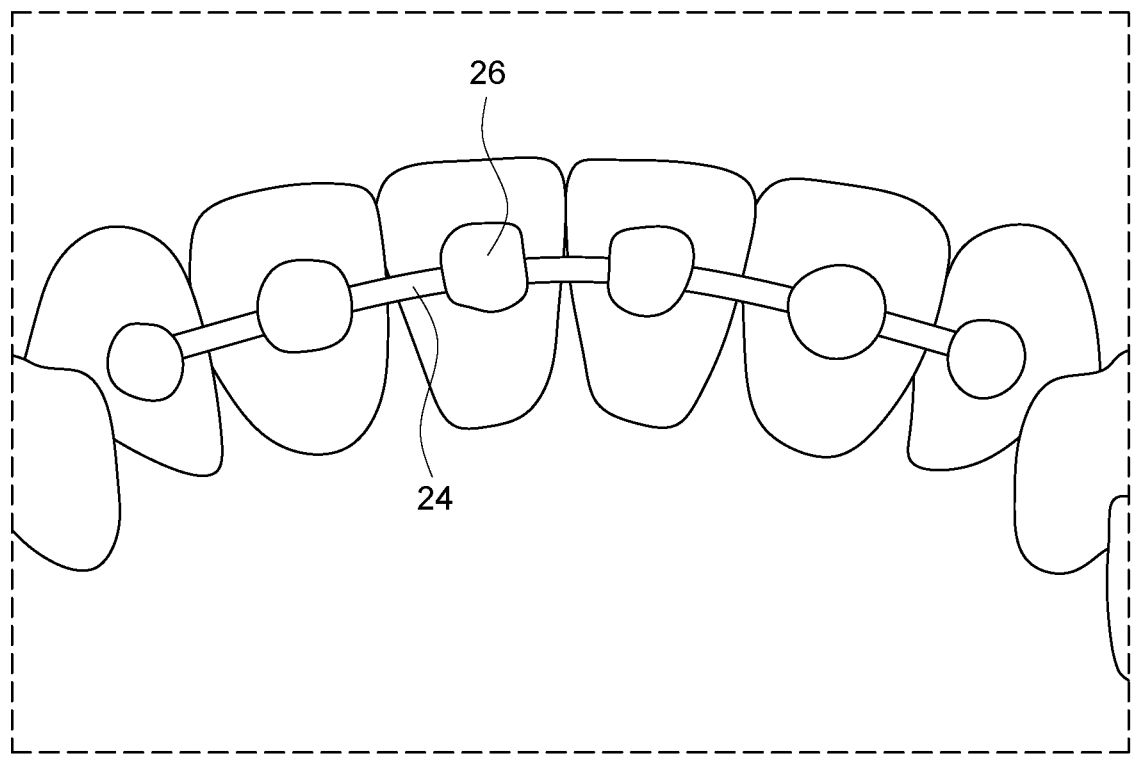
FIG. 9 is a front elevational view of lingual appliances and attachment mechanisms that may be utilized with any of the preferred embodiments of the invention of FIGS. 1A-4.
Figure 10:
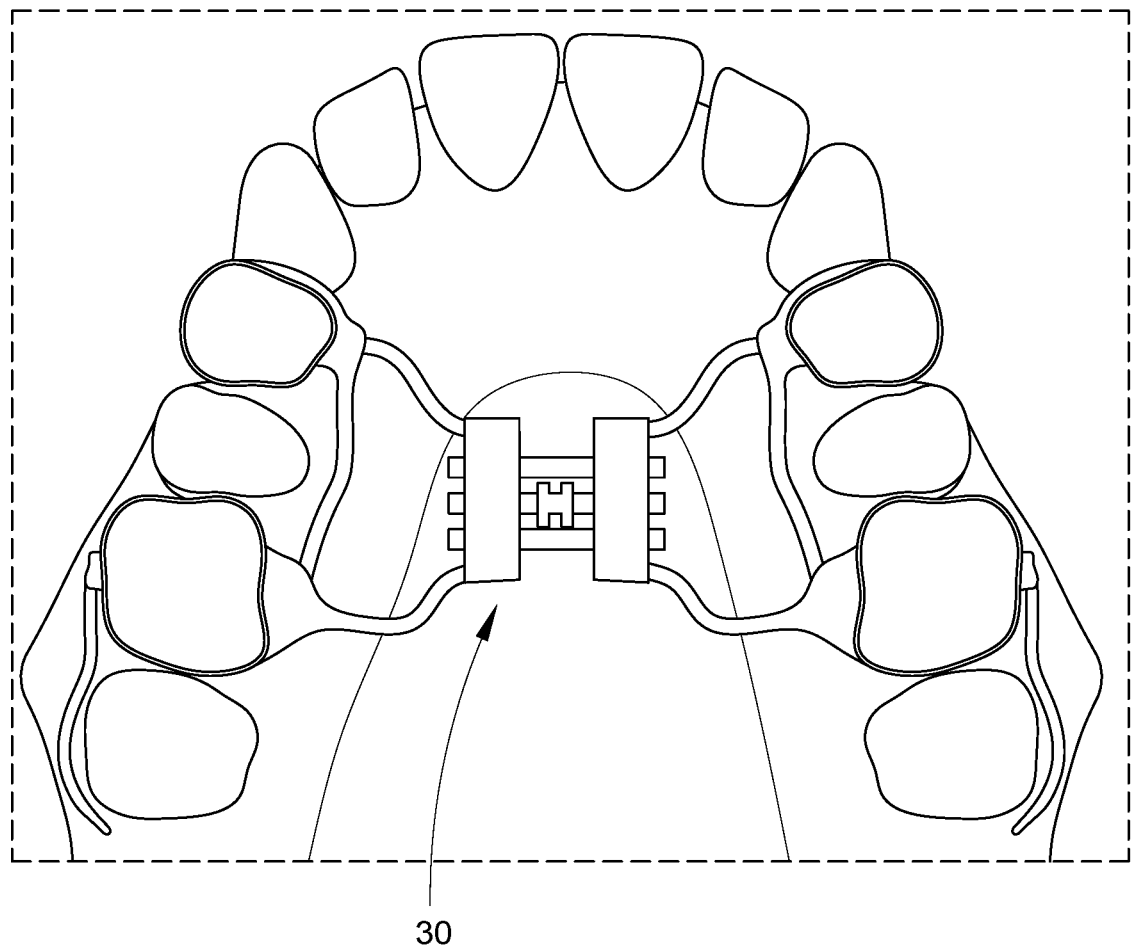
FIG. 10 is a bottom plan view of a palate expander that may be utilized with any of the preferred embodiments of the invention of FIGS. 1A-4.
Figure 11A:
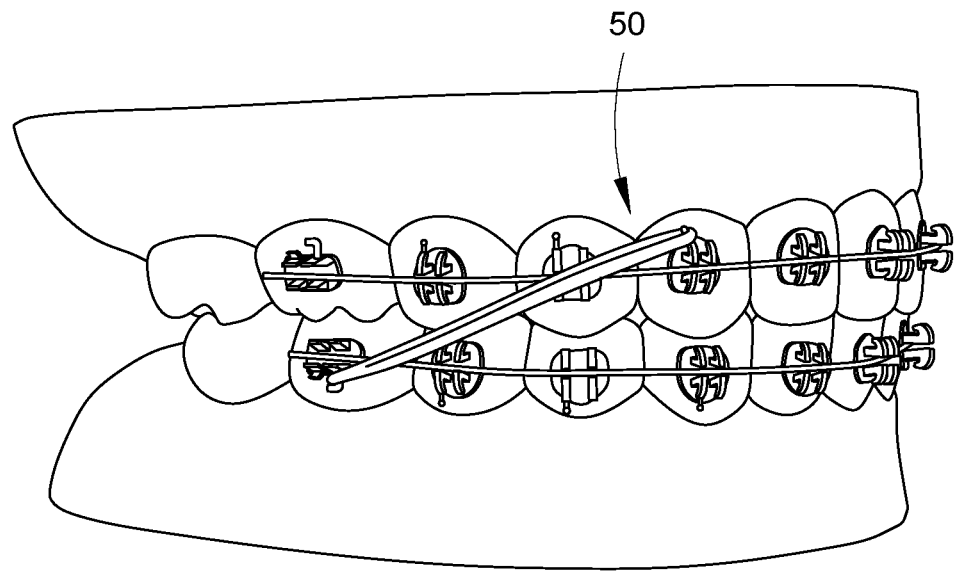
FIGS. 11A-11H are a side perspective views of intraoral elastics that may be utilized with any of the preferred embodiments of the invention of FIGS. 1A-4.
Figure 11B:
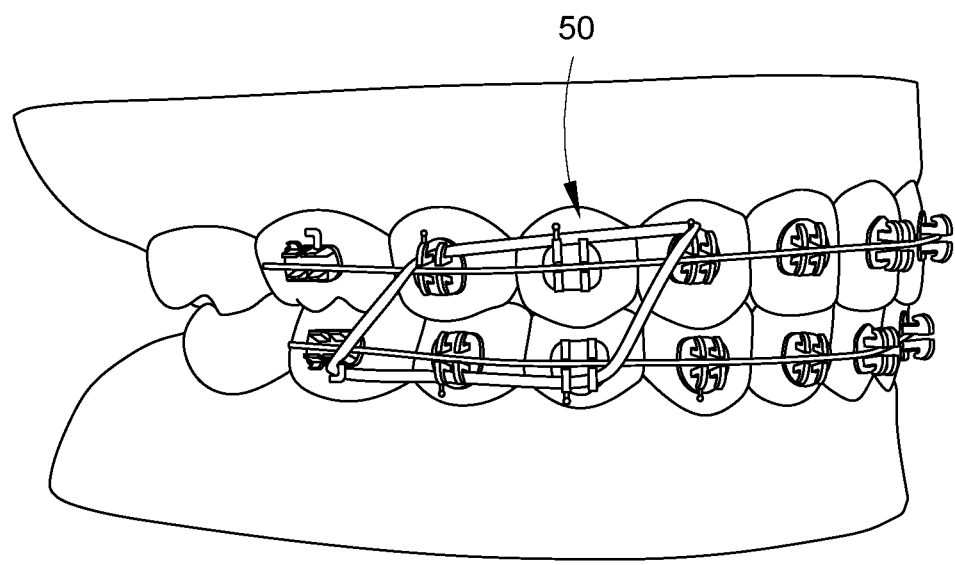
Figure 11C:
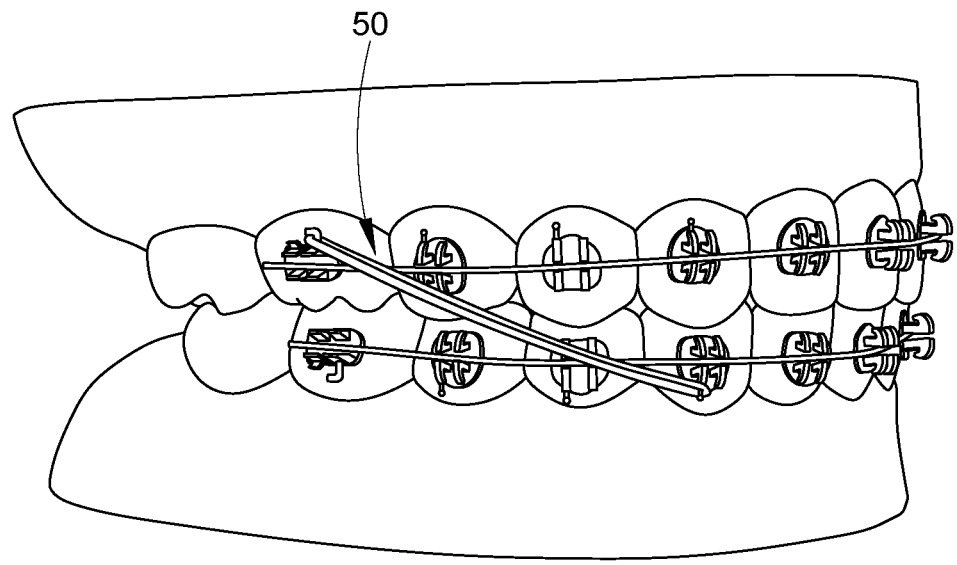
Figure 11D:
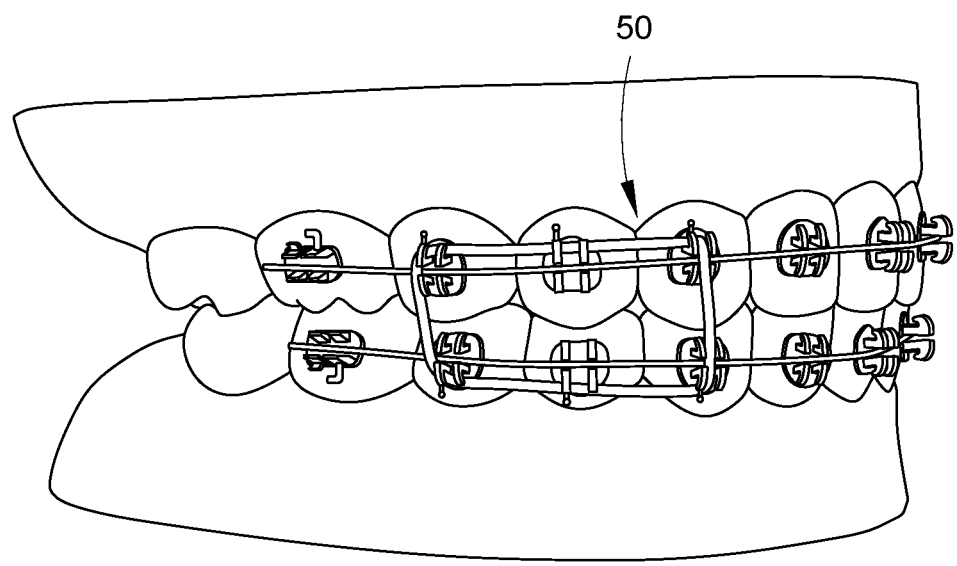
Figure 11E:
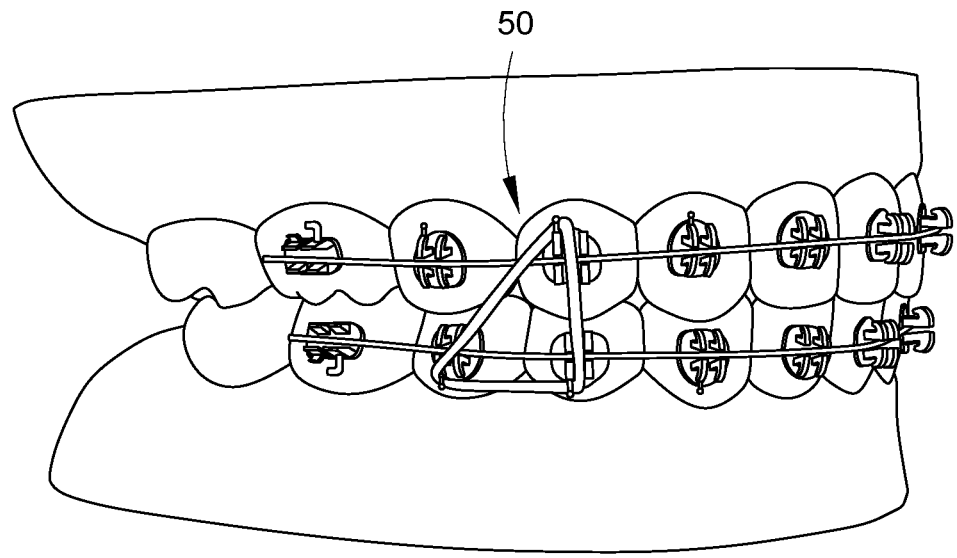
Figure 11F:
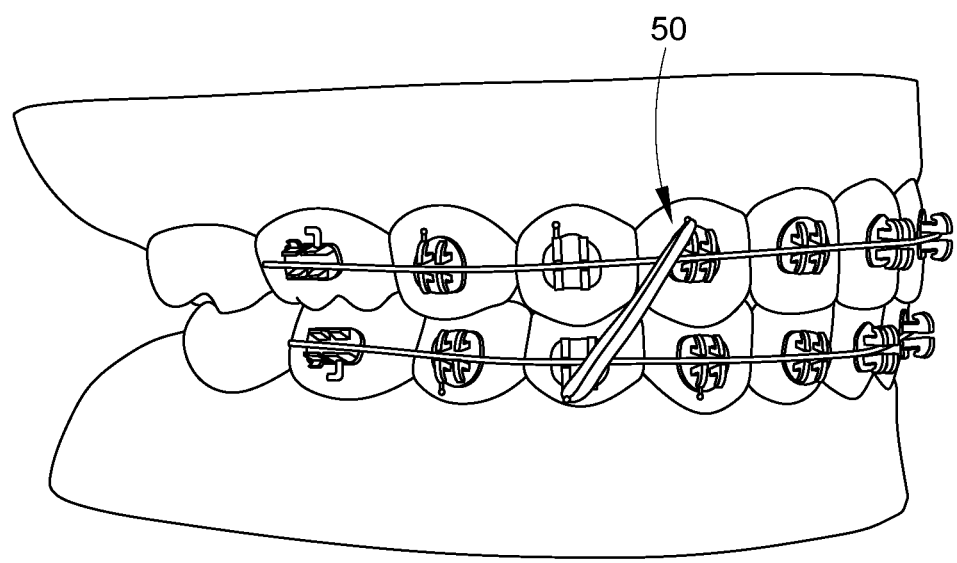
Figure 11G:
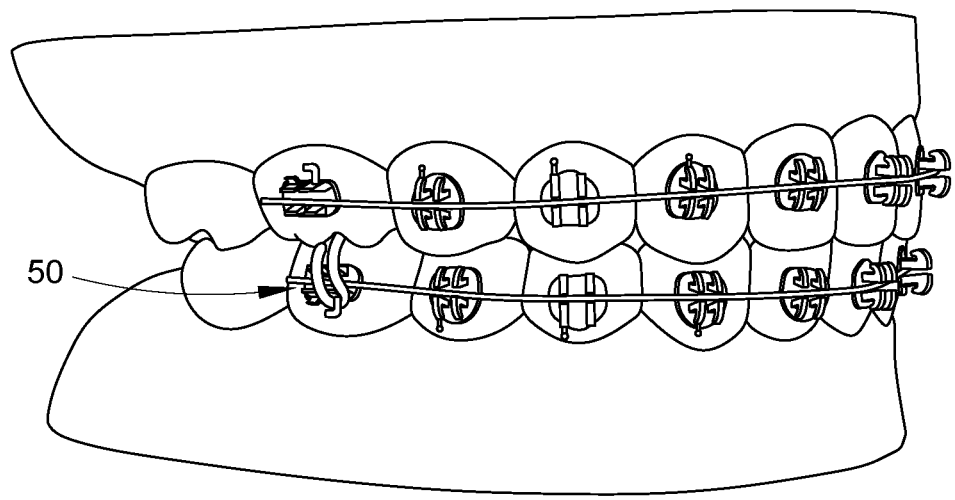
Figure 11H:
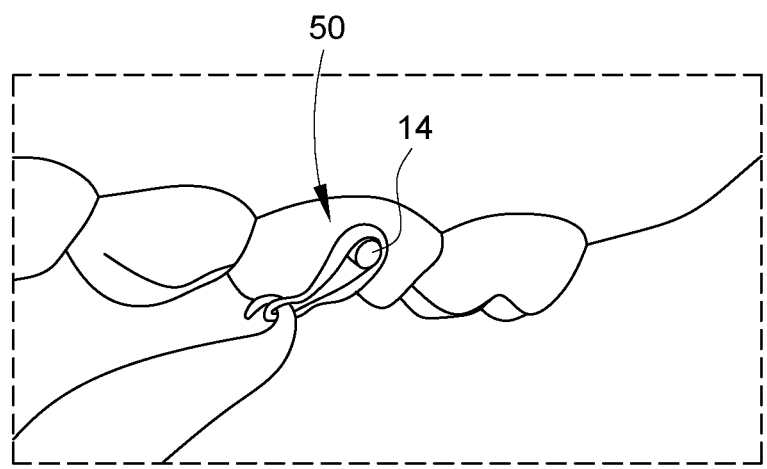

Referring to FIGS. 1-6, the systems 300, 400 may be configured to develop a treatment plan that includes a luggage loop 10. The luggage loop 10 is used to rotate a tooth using power chain elastics 12 and a lingual button 14. The systems 300, 400 preferably utilize closed space power chains, which means there is no space between the rings in the elastic, although the systems 300, 400 are not so limited. The lingual button 14 is preferably bonded to the lingual side of the rotated tooth based on the treatment plan developed by the systems 300, 400 and the images collected by the patient or during one of the office visits to the general dentist, preferably under the direction of the consultant orthodontist. The power chain is preferably tied over the wire next to the rotated tooth. The power chain is preferably stretched in between the teeth to the lingual side of the teeth as if it were dental floss. The power chain is pulled relatively tight and stretched over the lingual button 14 bonded on the lingual side of the rotated tooth. The force from the power chain will rotate the tooth. In FIG. 6, the tooth is being rotated mesially, although such rotation is not limited and the tooth may be otherwise manipulated, rotated or otherwise moved by orthodontic hardware under the direction of the treatment plan.

Referring to FIGS. 11A-11H, the preferred systems 300, 400 may utilize intraoral elastics 50, preferably to coordinate the patient's arches. Various common configurations of the intraoral elastics 50 are shown in FIGS. 11A-11H, wherein FIG. 11A may be considered to show Class II elastics, FIG. 11B may be considered to show Box Class II elastics, FIG. 11C may be considered to show Class III elastics, FIG. 11D may be considered to show Box Class III elastics, FIG. 11E may be considered to show triangle elastics, FIG. 11F may be considered to show vertical elastics, FIG. 11G may be considered to show crossbite elastics in a buccal view and FIG. 11H may be considered to show crossbite elastics in a lingual view. In the preferred embodiments, the crossbite elastics 50 usually utilize the lingual button 14 bonded to the lingual side of the patient's tooth. The elastic 50 is preferably placed over the lingual button 14 and a hook of another buccal bracket. The configurations shown in FIGS. 11A-11H are not limiting, but are generally common configurations of the elastics 50 that may be utilized with the preferred systems 300, 400.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present disclosure.

I claim:

1. A system for providing orthodontic treatment to a first patient during a current appointment following an initial appointment wherein a general dentist receives direction, including at least one of general and specific instructions from a consultant orthodontist, the system comprising:

a network configured to assign the consultant orthodontist to the general dentist during the current appointment, wherein the consultant orthodontist is located remote from the general dentist, the network including a central server with a patient database, the patient database including a first dental record of the first patient and a plurality of additional dental records of a plurality of additional patients, the network also including an analysis and prediction module, the analysis and prediction module configured to access the first dental record and at least one of the plurality of additional dental records, including a historical treatment plan, prior to initiation of the current appointment to compare and contrast the first dental record and the at least one of the plurality of additional dental records, including the historical treatment plan, to predict timing and outcome for the orthodontic treatment of the first patient and develop an original treatment plan based on the comparison of the first dental record with the at least one of the plurality of additional dental records, including the historical treatment plan during the initial appointment, the network further configured to receive current physical properties of the first patient's mouth during the current appointment, the current physical properties including distances between the first patient's teeth and a number of teeth based on current images for the current appointment, the analysis and prediction module configured to compare the current physical properties of the first patient's mouth to the first dental record, the plurality of additional dental records and initial physical properties of the first patient's mouth from the initial appointment to predict additional outcomes for the first patient and develop a current treatment plan, the initial physical properties include size and shape of a mandibular bone, size and shape of a maxillary bone, tooth root structure, including length and angle of the tooth root structure, dentition of the first patient's teeth, including presence of baby teeth, the first patient's age, periodontal issues of the first patient, profile of the first patient's face, including a distance between a nose and a chin of the first patient, and position of a tooth relative to a gum line of the first patient;

an orthodontic wire; and an adhesive configured to adhere the orthodontic wire to a lingual side of the first patient's teeth during the current appointment, the orthodontic wire and the adhesive being affixed to the lingual side of the first patient's teeth by the general dentist based on the current treatment plan.

2. The system of claim 1, further comprising:

a communication device configured to provide real-time conferencing between the general dentist and the consultant orthodontist.

3. The system of claim 1, wherein the analysis and prediction module utilizes artificial intelligence and machine learning to predict an impact of a prescribed treatment plan, including the original and current treatment plans, on the first patient's jaw and teeth and expected timeframes for changes, the analysis and prediction module also configured to predict a range of outcomes for the first patient, the first dental record including initial images taken by the first patient and received by the network from the first patient.

4. The system of claim 1, wherein the plurality of additional dental records includes dental records of actual patients and dental records of simulated patients.

5. The system of claim 1, wherein the plurality of additional dental records are comprised of dental records of simulated patients.

6. The system of claim 1, wherein the plurality of additional dental records are comprised of dental records of actual patients.

7. The system of claim 1, wherein the analysis and prediction module automatically develops the current treatment plan.

8. The system of claim 1, wherein the current images are collected by the first patient, the general dentist, a dental professional or a technician.

9. The system of claim 1, further comprising:

a scanner, camera or other imaging device configured to collect initial images for the initial appointment to develop the initial physical properties and the current images.

10. The system of claim 1, further comprising:

a camera configured to collect initial images before the initial appointment.

11. The system of claim 1, further comprising:

a camera configured to collect the current images before the current appointment.

* * * * *